United States Patent [19]
Noeske-Jungblut et al.

[11] Patent Number: 5,756,454
[45] Date of Patent: May 26, 1998

[54] COLLAGEN-INDUCED PLATELET AGGREGATION INHIBITOR

[75] Inventors: Christiane Noeske-Jungblut; Bernard Haendler; Joern Reiner Kraetzschmar; Wolf-Dieter Schleuning, all of Berlin, Germany; Alejandro Alagon, Cuernavaca; Lourival Possani, Cuernavaca; Delia Cuevas-Aguirre, Cuernavaca, all of Mexico

[73] Assignee: Schering Aktiengesellschaft, Berlin, Germany

[21] Appl. No.: 206,185

[22] Filed: Mar. 7, 1994

Related U.S. Application Data

[63] Continuation of Ser. No. 116,889, Sep. 7, 1993, abandoned, which is a continuation-in-part of Ser. No. 914,383, Jul. 17, 1992, abandoned, which is a continuation-in-part of Ser. No. 814,884, Dec. 31, 1991, abandoned, which is a continuation-in-part of Ser. No. 756,211, Sep. 5, 1991, abandoned.

[51] Int. Cl.[6] ............... A61K 38/00; C07K 1/00; A23J 1/00
[52] U.S. Cl. ............... 514/12; 530/350; 530/412
[58] Field of Search ............... 530/350; 514/12; 424/550; 435/69.1

[56] References Cited

U.S. PATENT DOCUMENTS 5,427,729  6/1995  Dubrow ............... 264/232

FOREIGN PATENT DOCUMENTS 0 040 149  11/1981  European Pat. Off. .
0 480 651  4/1992  European Pat. Off. .

OTHER PUBLICATIONS

1995 Pharmacia Biotech Catalog, pp. 307 and 314–315.
Baumgartner, Thromb. Haemostas., 37:1–16 (1977).
Hawiger, Human Pathol., 18:111–112 (1987).
Bevers et al., Thrombosis Research, 37:365–370 (1985).
Karniguian et al., Thrombosis Research, 32:593–604 (1983).
Smith et al., Thrombosis and Haemostasis, 65:678 (1991).
Munro et al., Blood Coagulationa and Fibrinolysis, 2:179–184 (1991).
Ribeiro et al., Experientia, 37:384–386 (1981).
Gasic et al., Biological Abstracts, vol. 76, Abstract No. 42969 (1983).
Connolly et al., J. of Biol. Chem., 267(10):6893–6898 (Apr. 5, 1992).
Kellet et al., J. of Biol. Chem., 267(10):6899–6904 (Apr. 5, 1992).
Sofer et al. Biotechniques Nov/Dec. 1983 pp. 198–203. (1983).

*Primary Examiner*—Keith D. Hendricks
*Assistant Examiner*—Lisa J. Hobbs
*Attorney, Agent, or Firm*—Millen, White, Zelano, & Branigan, P.C.

[57] ABSTRACT

The invention provides a protein which inhibits collagen-induced platelet aggregation, derived from *Triatoma pallidipennis*, and derivatives thereof. The protein is useful for inhibition of collagen-induced human platelet aggregation or of cancer with metastatic tumor cells.

30 Claims, 11 Drawing Sheets

COLLAGEN-INDUCED PLATELET AGGREGATION INHIBITOR

CROSS-REFERENCE TO RELATED APPLICATIONS

This application is a continuation of U.S. Ser. No. 08/116,889, filed Sep. 7, 1993 (now abandoned), which is a continuation-in-part of U.S. Ser. No. 07/914,383, filed Jul. 17, 1992 (now abandoned), which is a continuation-in-part of U.S. Ser. No. 07/814,884, filed Dec. 31, 1991 (now abandoned), which is a continuation-in-part of U.S. Ser. No. 07/756,211, filed Sep. 5, 1991 (now abandoned).

BACKGROUND OF THE INVENTION

Collagen is the most potent inducer known of human platelet aggregation. For instance, upon injury of the vessel wall and exposure to collagen, blood platelets rapidly adhere and become activated (Baumgartner, H. R. (1977) Thromb. Haemostas. 37, 1–16; Hawiger, J. (1987) Human Pathol. 18, 111–122).

Collagen-induced platelet aggregation of human platelets thus represents a risk factor for patients undergoing blood vessel-affecting procedures, e.g., angioplasty or sepsis, for those suffering myocardial infarction, for those recovering from treatment for myocardial infarction, inter alia.

Inhibitors of the collagen-induced platelet aggregation include synthetic oligopeptides corresponding to a collagen sequence, a snake venom protein and calin, a protein from the medicinal leech. The synthetic oligopeptides inhibit the collagen-induced platelet aggregation by binding to the platelets. A disadvantage is that they have an effect on platelet aggregation only in a relatively high dosage (about 70 µg/ml of the peptide yields 65% inhibition). See Bevers et al. (1985) "Collagen Derived Octapeptide Inhibits Platelet Procoagulant Activity Induced by the Combined Action of Collagen and Thrombin", Thrombosis Research, 37, 365–370; Karniguian et al. (1983) "Effect of a Collagen Derived Octapeptide on Different Steps of the Platelet/Collagen Interaction", Thrombosis Research 32, 593–604; and Caen et al. (1981) "Oligopeptides with specific inhibiting properties of collagen-induced aggregation, process for preparing the same and pharmaceutical compositions containing them", EPA 0 040 149. The inhibitory mechanism of the snake venom protein is still unknown. See Smith et al., "Identification of 50 kDalton snake venom proteins which specifically inhibit platelet adhesion to collagen." Thrombosis and Haemostasis (1991) 65, 678 (abstracts of the XIIIth Congress of the International Society on Thrombosis and Haemostasis, Jun. 30–Jul. 6, 1991 in Amsterdam). Calin reacts with collagen; it does not react with platelets. Thus, it is not specific for the platelet-collagen interaction, but it reacts also with collagen in the absence of platelets. See Munro et al. (1991) "Calin—a platelet adhesion inhibitor from the salvia of the medicinal leech", Blood Coagulation and Fibrinolysis 2, 179–184.

The publication of the European patent application EP 0 480 651 (Merck & Co. Inc., published 15 Apr. 1992) describes a protein having a molecular weight of about 16 kDalton and a capacity to inhibit collagen-induced aggregation of human platelets which protein is derived from the salivary gland of the leech *Haemaenteria officinalis*.

Other inhibitors of such aggregation are needed having varied or improved properties.

SUMMARY OF THE INVENTION

The invention provides a natural isolated, synthetically manufactured or recombinant protein which inhibits collagen-induced aggregation of mammalian platelets and which is isolated or isolatable from saliva of mammalian-blood sucking insects.

Primate platelets are more preferred, most preferred are human platelets.

The platelets from other species are also included, e.g., horses, sheep, cattle, pigs, dogs and cats.

Preferred is a protein of the invention which is isolated or isolatable from saliva of the subfamily (lat. Faminia) Triatomae and more preferred of *Triatoma pallidipennis*.

A further preferred aspect of the invention comprises a natural isolated, synthetically manufactured or recombinant protein which inhibits collagen-induced aggregation of mammalian platelets and which protein has a N-terminal amino acid sequence (amino acids 1–20 of SEQ ID NO:10)

Glu-Glu-Cys-Glu-Leu-Met-Pro-Pro-Gly-Asp-Asn-Phe-Asp-Leu-
1           5                    10                  14

Glu-Lys-Tyr-Phe-Ser-Ile (Amino Acids 1–20 of SEQ ID NO: 11)
15                 20

A further embodiment of the invention is a protein which inhibits collagen-induced aggregation of mammalian platelets which protein has the following amino acid sequence:
  a) the sequence in
     aa) SEQ ID NO:11,
     bb) SEQ ID NO:12 or
     cc) SEQ ID NO:13 or b) allelic modifications or muteins of the sequences in anyone of the SEQ ID NO: 11 to 13, which allelic modifications or muteins do not substantially affect the activity of the protein, or c) a protein according to anyone of the SEQ ID NO:11 to 13 or their modifications or muteins mentioned under b), comprising posttranslational modifications, which do not substantially affect the activity of the mature protein.

More preferred is a protein as mentioned before which is a recombinant protein.

The invention also comprises a protein which is free of glycosylation.

A further embodiment of the invention is a cDNA or DNA
  a) coding for a protein which has the following amino acid sequence:
     a) the sequence in
        aa) SEQ ID NO:11,
        bb) SEQ ID NO:12 or
        cc) SEQ ID NO:13 or b) coding for a protein which has a sequence of amino acids according to anyone of the SEQ ID NO:11 to 13 with at least one allelic modification or a mutein which does not substantially affect the activity of the mature protein encoded by the corresponding cDNA or DNA sequence.

The protein of the invention comprises a mature protein and a preprotein which has as signal sequence preceding the N-terminal part of the mature protein. The signal sequences can be seen in FIGS. 13a and 13b and they can be recognized by their negative enumeration. They start with Met-Lys-Val-Ile-Ile- and end with -His-Ala-Phe-Ala. The signal sequence is responsible for the penetration of the membrane after protein biosynthesis. The protein which is secreted is the mature protein, starting with Glu-Glu-Cys-Glu-Leu-... The signal sequence is cleaved prior to secretion.

The invention preferably comprises a cDNA or DNA with the following nucleotide sequence:
a) the nucleotide sequence in
aa) SEQ ID NO:14,
bb) SEQ ID NO:15 or
cc) SEQ ID NO:16 or b) a sequence of nucleotides according to any one of the SEQ ID NO:14 to 16 with at least one allelic modification or a mutein which does not substantially affect the activity of the mature protein which is encoded by the corresponding nucleotide sequence.

A further aspect of the invention is a vector comprising a cDNA or DNA as mentioned before, further comprising a suitable signal peptide, a suitable promoter and, if need be, a suitable enhancer. Vectors are described in detail in the literature of the Examples and also in the European publications EP 0 480 651, 0 462 632 and 0 173 177.

A further embodiment of the invention is an eukaryotic or prokaryotic host cell transformed with a vector as mentioned above.

The most preferred host cell is a baby hamster kidney cell. As the legal requirements make a deposition of such a cell impossible, the plasmid expression construct comprising the DNA of Sequence Identifier 1 has been deposited on 2 Sep. 1992 and has been assigned the number DSM ...

The invention additionally comprises a method of producing a protein according to the invention which method comprises
culturing a host cell transformed by a vector comprising the gene coding for the protein, and
isolating and purifying the protein. The concrete embodiments are described in the Examples of the invention, the general method can be deduced from the state of the art mentioned in the specification, especially in the Examples of the invention.

In a preferred aspect, this invention provides an inhibitor of the collagen-induced aggregation of human platelets. The new specific inhibitor is naturally occurring, is a protein (i.e., not an oligopeptide) and also inhibits the tumor cell-collagen interaction. Such an inhibitor is present in the saliva of the blood-sucking bug *Triatoma pallidipennis*. See Example 1.

Thus, this invention relates to a purified and isolated protein which inhibits collagen-induced aggregation of human platelets. The protein is isolatable from *Triatoma pallidipennis*. The invention also relates to pharmaceutical compositions containing a protein and methods of using the latter for treating thrombotic lesions or for preventing reocclusion after treatment of myocardial infarction, and for treatment of progression of metastasis; inter alia.

Thus, this invention provides a valuable pharmacologically active substance, e.g., a new protein which specifically inhibits the collagen-induced platelet aggregation with a high specific activity; a new protein which specifically interferes with the platelet-collagen interaction without causing release of intraplatelet constituents, e.g., ATP, which have undesirable side effects by themselves; a new protein for pharmaceutical use in treating atherosclerotic and thrombotic diseases or in preventing reocclusion after treatment of myocardial infarction; a new protein which interferes with tumor cell-collagen interaction and which can be used, e.g., to prevent tumor cell metastasis.

An investigation of the characteristics and properties of the inhibitor yielded the following results:

1) The inhibitor is not a fibrinogen-receptor antagonist, because experiments with increasing fibrinogen concentrations showed no influence on the inhibitory activity. See Example 3.
2) It is not a thromboxane-antagonist, because it prevents the collagen-induced aggregation of platelets pretreated with aspirin but not the U46619 (a thromboxane mimeticum) induced aggregation. See Example 4.
3) It is probably not an inhibitor of the protein kinase C mediated signal transduction pathway, because the aggregation induced by phorbol esters (phorbol-12-myristate-13-acetate) is not inhibited. See Example 4.
4) It inhibits the release-reaction of collagen-treated platelets. See Example 5.
5) It does not inhibit the platelet aggregation induced by thrombin or ADP. See Example 6.
6) The inhibitor does not react with collagen. While preincubation of the inhibitor with collagen does not yield an increased inhibitory activity, a prolonged incubation of the platelets with the inhibitor leads to a higher inhibitory potency. See Example 7.
7) The inhibition of platelet aggregation becomes reversible by the addition of a large amount of collagen. See Example 7.
8) Protease inhibitors do not have measurable influence on the activity. See Example 8.
9) The inhibitory activity is higher in the presence of $Mg^{2+}$-ions. See Example 9.
10) The inhibitor prevents the adhesion of platelets to a collagen matrix in a dose-dependent manner. See Example 10.

These results strongly imply that the inhibitor is a collagen receptor antagonist of high specific activity, e.g. $IC_{50}=2.5$ μg per ml of the "Superose"-pool fraction described below (based on partially purified inhibitor) and $IC_{50}=50$ nmol/l of the highly purified protein (purified according to the consecutive steps described in the Examples 2 and 15).

11) The inhibitor was incubated with trypsin bound to a Sepharose-matrix. The inhibitory activity was totally lost by proteolytic digestion. See Example 11, showing that the inhibitor is a protein.
12) The inhibitor is not cleavable by collagenase. See Example 12.
13) According to gel filtration chromatography in the presence of 150 mM NaCl, the inhibitor has a molecular weight of 20 kDa±5 kDalton, i.e., about 20 kDalton. See Example 13. The value of the non-glycosylated protein (See SEQ ID NO: 11) calculated for the cDNA sequence is 18,923 Dalton.
14) The inhibitor prevents the adhesion of highly metastatic tumor cells (MTLn3) to collagen in a dose dependent manner. See Example 14.

The inhibitor of this invention does not bind to (or react with) collagen, does bind to platelets, and does not cause flocculation of collagen.

The collagen inhibitor of this invention can be routinely isolated from saliva of the blood-sucking bug *Triatoma pallidipennis*, e.g., as described in the examples herein. Conventional saliva harvesting methods are fully applicable to provide the starting material saliva. The bug *Triatoma pallidipennis* is prevalent and thus readily available in Central and South America. It is known as a vector for *Trypanosoma cruzi*.

In another aspect of this invention, there are provided DNA sequences, vectors containing theses sequences, cells containing said vectors, methods of recombinantly producing proteins and antibodies to the proteins of this invention. Also provided are isolated and/or recombinant DNA sequences (e.g., genomic or cDNA) coding for a protein (e.g., naturally occurring) which inhibits collagen-induced aggregation of human platelets. In a still further aspect, the invention provides recombinantly produced proteins of this invention, e.g., having the sequences disclosed herein.

By the term "isolated" is meant that the inhibitor of this invention or other entity is present in a form separated from (purified from) components with which it is naturally combined or with which it is produced recombinantly or synthetically. All degrees of such isolation or purification are included generically. Preferred are degrees of isolation or purification whereby the inhibitor is useful for pharmaceutical purposes. For example, such degrees of isolation (e.g., activities or purities) can be routinely achieved by chromatographic techniques such as those used in the examples. Further purifications, e.g., to homogeneity, can be routinely achieved using conventional methods, such as those described in the following texts:

Methods of Enzymology, Volume 182, Guide to Protein Purification, ed. Murray P. Deutscher, Academic Press 1990;

Protein Purification Applications—A Practical Approach. ed. E. L. V. Harris and S. Angel, IRL-Press 1990;

Protein Purification, Principles and Practice, Robert Scopes, Springer-Verlag 1982; and Protein Purification, Principles, High Resolution Methods and Applications, ed. J.-C. Janson and L. Ryden, VCH publishers 1989.

Purity can be determined by any one of a number of routine methods, e.g., SDS polyacrylamide gel electrophoresis, analytical HPLC, etc. Purified inhibitor can be used to determine the amino acid sequence of the protein according to methods fully routine to one of ordinary skill in the art. Hewick, R. M. et al. (1981) J. Biol. Chem. 256, 7990–7997.

Synthetically manufactured proteins can be prepared according to J. M. Steward and J. D. Young (1984) Solid Phase Peptide Synthesis, Pierce Chem. Company, Rockford, Ill., and according to Methoden der Organischen Chemie (Houben/Weyl), Vol. 15, Nos. 1 and 2, E. Wünsch (ed.), Thieme Verlag Stuttgart, 1974.

The protein of this invention includes not only the protein isolated from the exemplified species of insect, but also any other organism which may contain said inhibitor. In addition, the inhibitor of this invention includes inhibitors having related structure, e.g., a collagen-induced platelet aggregation inhibitor isolated from another organism which has a substantially similar amino acid sequence.

Since this protein is isolated from a biting insect, and its natural utility is apparently to keep a bite wound in a host unobstructed by blood clots for an extended period of time in order to effect the intake of a blood meal, it is quite likely that other such collagen-induced platelet aggregation inhibitors will be found in the saliva of other blood-sucking organisms, especially insects, e.g., in other cone-nosed Reduviid bugs of the subfamily Triatominae, such as *Triatoma infestans, T. dimidiata, T. maculata, Rhodnius prolixus, Panstrongylus megistus* and *P. infestans*.

Proteins of this invention include monomeric, single chain molecular forms, i.e., those not covalently or noncovalently bonded to other polypeptide chains. This invention also encompasses other molecular forms of the protein, e.g., dimers or other oligomers, tertiary structures formed with other polypeptides, fragments of the protein, etc. Both glycosylated and unglycosylated forms are included, both forms being routinely preparable by expression from, e.g., mammalian (glycosylated) or bacterial cells (unglycosylated), respectively.

The amino acid sequence of the inhibitor of the present invention can be used to determine the sequence of suitable DNA probes, which can be used for finding new inhibitors, e.g., in other species. Such probes can be routinely synthesized, e.g., using automated DNA synthesizers, and screening of genomic or cDNA libraries is similarly routine for one of ordinary skill in the art (see International Publication WO 90/07861 dated 26 Jul. 1990).

For example, the invention relates to DNA sequences as disclosed in SEQ ID NOS:1–6, 7–10 and 17–19. Still further, the invention relates to DNA sequences coding for muteins as defined above. The sequence for the −18 to +5 region in SEQ ID NOS: 13, 16 and 19 are deduced from the corresponding full length cDNA sequences of inhibitors 1 and 2.

Therefore, the present invention also includes the DNA sequence corresponding to (coding for) both the natural DNA sequence (gene) for the inhibitor, when isolated from the natural environment, e.g., in solution or on a vector, as well as muteins thereof, either naturally occurring, e.g., in other species, in isolated form or synthetic, e.g., as produced by site-directed mutagenesis. Methods of screening genetic libraries of various species with a suitable probe are conventional in the art. Methods for producing muteins are also routine and conventional for one of ordinary skill in the art, as are screening methods for testing the efficacy of such new proteins, e.g., as described herein.

Allelic modifications as mentioned before comprise alteration in the sequence of the nucleotides or amino acids, alteration of the genotype or phenotype. At least one nucleotide or one amino acid can be substituted, deleted or inserted.

Most deletions, insertions and substitutions in particular, are not expected to produce radical changes in the characteristics of the protein of the invention. As it is difficult to predict the exact effect of the substitution, deletion, or insertion in advance, the comparison of the functions of the mutated protein with the characteristic functions of the protein of the invention clarify whether the altered protein has a comparable activity.

The genetic code is degenerate; that is, most amino acids are coded for by more than one codon of three nucleotides. Accordingly, allelic variation in the nucleotide sequence may or may not alter the amino acid sequence. Therefore, allelic variations are primarily on the DNA level and may also exist secondarily on the level of the amino acid sequence.

The DNA sequence coding for the protein of the invention can be modified by conventional techniques to produce variations in the final protein of the invention which still have substantially the same activity as the protein of the invention. The activity is measured according to Example 1. Thus, one or more amino acids, for example 1, 2, 3, 4, 5, 6, 7, 8, 9, 10 ... up to 15 amino acids, can be added, substituted or removed without substantially affecting the activity of the protein of the invention. Substitutions can generally be made in accordance with the following Table 1 when it is desired to modulate finely the amino acid sequence of the protein of the invention.

Substantial changes in function or immunological identity are made by selecting substitutions that are less conservative than those in Table I, i.e., selecting residues that differ more significantly in their effect on maintaining (a) the structure of the polypeptide backbone in the area of the substitution, for example, as a sheet or helical conformation, (b) the charge or hydrophobicity of the molecule, or (c) the bulk of the side chains.

TABLE 1

Normal substitutions of amino acids in a protein

| Original Residues | Exemplary Substitutions |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

Muteins are defined by homology between two compared proteins. The term "homology" comprises similarities of the amino acids and gaps in the sequences of both compared sequences. Similarity of amino acids is defined for example in Table 1.

Preferably the protein has a sequence of amino acids having a homology of at least 60%, more preferred, at least 80%, much more preferred at least 90% and most preferred at least 95% of the sequence shown in one of the SEQ ID NO:11 to 13.

As mentioned before, the invention comprises variation of the DNA. These sequences hybridize under stringent condition to the DNA sequence defined in one of the SEQ ID NO:14 to 16. Preferably the cDNA or DNA has a sequence of nucleotides having a homology of at least 60%, more preferred at least 80%, much more preferred at least 90% and most preferred at least 95% of the sequence shown in one of the SEQ ID NO:14 to 16. The homology can be measured by hybridization described in R. Knippers, Molekulare Genetik, 1982, third edition, Georg Thieme Verlag Stuttgart, New York.

Suitable muteins, either synthetic or naturally occurring (in isolated form), are those having at least a fraction, e.g., at least 5%, preferably at least 50%, most preferably at least 90% of the biological activity, e.g., collagen-induced platelet aggregation inhibition, of naturally occurring, isolated *T. pallidipennis* inhibitor as described herein.

Suitable muteins will differ from the natural proteins in any modification possible, including deletion, addition and/or substitution of one or more amino acids as long as substantial biological activity is retained; preferably the biological activity is substantially unaffected. Such muteins are equivalents of the natural proteins. Similarly, equivalents of the DNA sequences disclosed herein include allelic variants, sequences coding for the equivalent muteins discussed herein and DNA sequences which are homologous therewith.

By "post-translational variations" as mentioned above is meant variations during or after translation, such as glycosylation, formation of disulfide bridges and chemical modifications of amino acids.

Glycosylation is one of the major biosynthetic functions of the endoplasmic reticulum and/or Golgi apparatus. The sequence and branching of the oligosaccharides formed in the reticulum can be altered in the Golgi apparatus, the lysosomes or plasma membrane. The oligosaccharides can be N-linked oligosaccharides (asparagine linked) or O-linked oligosaccharides (serine, threonine or hydroxyllysine linked). The glycosylation is dependent on the producing cell type and the species from which the cell type derives. The amount and form of glycosylation can be influenced by compounds as described in European Patent Application EP 0 222 313. Changes in glycosylation may affect the function of the protein.

Normally the mature protein of the invention is glycosylated.

Proteins often form covalent intrachain bonds. These disulfide bonds are formed between cysteine-SH amino acids in the folded protein or in the protein which folds during translation. The bonds stabilize the three-dimensional structure of the protein. Such disulfide bonds are rarely formed in protein molecules that are still in the cell cytosol because the high intracellular concentration of the -SH reducing agent glutathione breaks most of such bonds. Once the proteins are outside the cytoplasm, are secreted or are on the cell surface, they often form additional covalent intrachain bonds.

Furthermore, the amino acids may be altered as described in PCT Application WO 91/10684. Other alterations of the side chains of the amino acids are possible.

A preferred homology is at least 90%, more preferred at least 95%, much more preferred at least 98% and most preferred the alteration of one or two amino acids.

The protein of the invention has at least a purity of 40%, preferably at least 60%, more preferably at least 80% and most preferably at least 90%. The purity is defined by the amount of the protein of the invention in relation to the total amount of protein. Using the purification in two steps, first by Sepharose gel filtration (see Example 2) and second by HPEC (see Example 15) no other protein beside the proteins of the invention are detectable by methods described in the Example 15.

Furthermore, the invention includes fragments of the thrombolytic polypeptide, e.g., having similar functions or isolated subfunctions, e.g., isolated epitopes, active sites, fibrin and/or fibrinogen binding regions, etc. Single chain forms of the inhibitor are preferred.

Further, the invention comprises binding molecules, single chain proteins, antibodies or fragments thereof, recognizing specifically domains on the mature protein of the invention.

The invention also relates to antibodies and antibody-producing cell lines, in particular monoclonal antibodies and cell lines, which can routinely be produced using the purified proteins of this invention (e.g., of the sequences SEQ ID NO:11 to 13), e.g., according to the highly conventional K öhler and Milstein method involving conventionally immunizing mice with the purified protein of the invention as immunogen. The invention also relates to fragments of said antibodies, e.g. antibody fragments containing a domain which binds to an epitope on the inhibitor protein and to synthetic binding domains, e.g., mimotopes, specifically recognizing domains on the proteins of this invention.

The best mode of the invention is the protein mentioned in SEQ ID NO:11, expressed in transfected baby hamster kidney cells.

The invention additionally comprises a method of purification of the protein of the invention comprising (a) a step of gel filtration using "Superose 12" (See Example 2) and (b) a step of High Performance Electrophoresis Chromatography System (See Example 15).

Utility of the Compounds

The proteins of the invention exhibit pharmacological activity and are, therefore, useful as pharmaceuticals. They can be used in a pharmaceutical composition comprising a protein of the invention in association with pharmaceutically acceptable diluent or carrier. Additionally, the invention comprises a pharmaceutical composition comprising a pharmaceutically active protein according to the invention and a pharmaceutically acceptable salt or a pharmaceutically acceptable carrier. In particular, the protein of the invention shows inhibition of collagen-induced platelet aggregation and inhibition of adhesion of tumor cells, preferred of metastatic tumor cells, to collagen.

Pharmaceutical for Inhibition of Platelet Aggregation

The proteins of the invention are useful for the treatment of atherosclerotic or thrombotic disease lesions or for preventing reocclusion after treatment of myocardial infarction. Thus, the proteins of the invention can be used as an antiatherosclerotic and antithrombotic agent in mammals, including humans, e.g., to treat atherosclerotic/thrombotic lesions, for example due to rupture of atherosclerotic plaques or those due to perturbation or removal of endothelium, e.g., in sepsis or transplants or to treat unstable angina. They can also be used to prevent reocclusion after treatment of myocardial infarction by fibrinolysis or by angioplasty (PTCA). If fibrinolytic therapy (with streptokinase, t-PA or other plasminogen activators) is applied to treat myocardial infarction the proteins of the invention can be used as an adjuvant agent to prevent reocclusion of the blood vessel. Treatment of myocardial infarction with a balloon catheter (PTCA) also injures the vessel wall and this may lead to formation of a new thrombus. This can be prevented by administering the proteins of the invention during and after the procedure. In addition, the proteins are also employable in other angioplasty applications.

The test system for showing that proteins inhibit platelet aggregation is described in Example 1. The proteins of the invention show a significant inhibition of platelet aggregation in a concentration of 0.5 to 50 µg protein saliva in 0.5 ml or 0.5 to 250 µg protein in 0.7 ml of purified protein (only purified according Example 2).

The test of the most preferred protein, the protein of SEQ ID NO:1, shows a value of the $IC_{50}$ of 50 nmol/l of highly purified protein according to the Examples 2 and 15. The proteins of the invention show the inhibition of platelet aggregation at concentrations of from 5 nmol/l to about 1,000 nmol/l.

The results from the in vitro test systems indicate that the proteins of the invention can be used as a medicament or can be used for medical treatment. The test results can be transferred from the in vitro system to the in vivo system, because it is an established system in this field. R. J. Shebuski et al. (1990) Thrombosis and Haemostasis, 64: 576–581.

Details of such uses, e.g., dosage ranges, regimes of administration (preferably, oral or parenteral), etc., can be routinely determined, e.g., by analogy to and/or routine comparison with other antithrombotic agents such as t-PA, streptokinase, or other platelet-aggregation inhibitors such as Iloprost, etc.

The proteins of the invention are administered by intraperitoneal injections which are given daily or at 2 to 3 times a week. When animals receive daily injections to achieve a blood concentration of 100 nmol/l, they have a reduced platelet aggregation.

No serious side effect are monitored under these conditions.

The proteins of the invention show this inhibition of platelet aggregation in mice at daily dosages to achieve a blood concentration of from about 10 nmol/l to 1,000 nmol/l.

Thus, the invention provides a) the use of a protein of the invention for manufacture of a medicament for treatment of atherosclerotic or thrombotic disease or for preventing reocclusion after treatment of myocardial infarction (the proteins are useful for prophylactically working medicaments.)

b) a method of treatment of atherosclerotic or thrombotic disease or for preventing reocclusion after treatment of myocardial infarction, which comprises administering of a disease-suppressing effective amount of the protein of the invention to a patient in need of such treatment;

c) a pharmaceutical composition for treatment of atherosclerotic or thrombotic disease or for preventing reocclusion after treatment of myocardial infarction which comprises a protein of the invention and a pharmaceutically acceptable carrier or diluent.

For these indications the appropriate dosage will, of course, vary depending upon, for example, the compound of the invention employed, the host, the mode of administration and the nature and severity of the condition being treated. However, in general, satisfactory results in animals are indicated to be obtained at daily dosages to achieve a blood concentration of from 10 to 1,000 nmol/l, preferred at daily dosages of from 30 to 300 nmol/l.

The proteins of the invention may be administered by any conventional route, in particular enterally, orally, e.g. in the form of tablets or capsules or parenterally, e.g. in the form of injectable solutions or suspensions.

The protein of SEQ ID NO:11 is the preferred compound.

The present invention provides pharmaceutical compositions comprising compounds of the invention in association with at least one pharmaceutical carrier or diluent. Such compositions may be manufactured in conventional manner. See Remington's Pharmaceutical Science, 15$^{th}$ ed. Mack Publishing Company, Easton, Pa. (1980).

Pharmaceutical for Treatment of Metastatic Tumor Cells

The inhibitor of this invention can also be used to prevent metastasis of tumor cells by blocking their passage through the connective tissue. It is applicable to prevent metastasis of all invasive tumors, e.g., melanoma. The following is offered without wishing to be bound by theory. During metastasis, the tumor cells have to penetrate through the base membrane and interstitial matrix. Both matrices are rich in various collagen types. The dissemination of the tumor cells requires interaction with these proteins. Evidence for the role of the collagen receptor (VLA 2) in this interaction is provided by, e.g., Chan et al. (1990, Science 2, 1600–1602) who cloned the VLA 2 positive tumor cells which formed substantially more metastatic tumor colonies. Kramer and Marks (1989) J. Biol. Chem. 264, 4684–4688 were able to block the attachment of human melanoma cells to collagen by an antibody to VLA 2. See also: PA US 73234708-A "Monoclonal antibody against platelets— which inhibit platelet reaction with collagen and are used for detecting and treating cancer", U.S. Dept. Health and Human Services. The inhibitor of this invention, being a collagen receptor antagonist prevents the interaction of tumor cells with the surrounding matrix and thus inhibits metastasis.

The inhibitor of this invention is also employable as a standard for determining the effectiveness of new inhibitors which can be developed, e.g., by modification of the structure of the present inhibitor through standard mutagenesis, directed mutagenesis, e.g., deletions and/or insertions of sequences, protein modifications, etc. The inhibitor of this invention can also be used as a standard antithrombotic in screening procedures which test for the effectiveness of various compounds as an antithrombotic, or as a standard for determining the effectiveness of compounds which block the effects of such collagen-induced platelet aggregation, e.g., in patients suffering from clotting deficiencies.

The test system for showing that proteins display adhesion-inhibition of metastatic tumor cells to collagen is described in Example 14. The proteins of the invention show a significant adhesion-inhibition of metastatic tumor cells to collagen in a concentration of 1 to 100 µg protein saliva in 0.5 ml or 1 to 500 µg protein in 0.5 ml of purified protein (only purified according Example 2).

The test of the most preferred protein, the protein of SEQ ID NO: 11, shows a value of the $IC_{50}$ of 100 nmol/l of the highly purified protein according to the Examples 2 and 15. The proteins of the invention show the adhesion-inhibition of metastatic tumor cells to collagen at concentration of from 10 to 2,000 nmol/l.

The results from the in vitro test systems indicate that the proteins of the invention can be used as a medicament or can be used for medical treatment. The test results can be transferred from the in vitro system to the in vivo system, because it is an established system in this field. Chan et al. (1990), Science, 2: 1600–1602.

The proteins of the invention can be administered during and after surgical operations of the primary tumor to prevent formation of metastasis by detached tumor cells which may enter the blood stream during operation. These anti-metastatic effects can be investigated in an "experimental" and "spontaneous" animal model as described by Chan et al. (1990), Science, 2: 1600–1602.

The proteins of the invention are administered by intra-peritoneal injections which are given daily or at 2 to 3 times a week. When animals receive daily injections to achieve a blood concentration of 200 nmol/l, they have a reduced adhesion of metastatic tumor cells measured by counting the value of centers of settled metastatic cells.

No serious side effect are monitored under these conditions.

The proteins of the invention show this adhesion-inhibition of metastatic tumor cells to collagen in mice at daily dosages to achieve a blood concentration of from 20 to 2,000 nmol/l, preferred concentrations of from 60 to 600 nmol/l.

The proteins of the invention are, therefore, useful for the treatment of cancer, preferred of cancer with metastatic tumor cells, most preferred of cancer with highly metastatic tumor cells.

The invention provides
a) the use of a protein of the invention for manufacture of a medicament for treatment of cancer with metastatic tumor cells (the proteins are useful for prophylactically working medicaments administered before e.g., surgical removal of tumors);

b) a method of treatment of cancer with metastatic tumor cells, which comprises administering of a disease suppressing effective amount of the protein of the invention to a patient in need of such treatment;

c) a pharmaceutical composition for treatment of cancer with metastatic tumor cells which comprises a protein of the invention and a pharmaceutically acceptable carrier or diluent.

For these indications the appropriate dosage will, of course, vary depending upon, for example, the compound of the invention employed, the host, the mode of administration and the nature and severity of the condition being treated. However, in general, satisfactory results in animals are indicated to be obtained at daily dosages to achieve a blood concentration of from 20 to 2,000 nmol/l, preferred at daily dosages of 60 to 600 nmol/l.

The proteins of the invention may be administered by any conventional route, in particular enterally, orally, e.g. in the form of tablets or capsules or parenterally, e.g. in the form of injectable solutions or suspensions.

The protein of SEQ ID NO:11 is the preferred compound.

The present invention provides pharmaceutical compositions comprising compounds of the invention in association with at least one pharmaceutical carrier or diluent. Such compositions may be manufactured in conventional manner. See Remington's Pharmaceutical Science, 15$^{th}$ ed. Mack Publishing Company, Easton Pa. (1980).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

DESCRIPTION OF THE DRAWINGS

Various other objects, features and attendant advantages of the invention will be more fully appreciated as the same becomes better understood when considered in conjunction with the accompanying drawing, in which like reference characters designate the same or similar parts throughout the several views, and wherein.

The SEQ ID NOS refer to the following

DNA sequence (SEQ ID NO:1) of the subcloned PCR product of type 1 and the deduced amino acid sequence (SEQ ID NO:2);

DNA sequence (SEQ ID NO:3) of the subcloned PCR product of type 2 and the deduced amino acid sequence (SEQ ID NO:4);

DNA sequence (SEQ ID NO:5) of the subcloned PCR product of type 3 and the deduced amino acid sequence (SEQ ID NO:6);

complete DNA sequence (SEQ ID NO:7) of the cloned cDNA of inhibitor 1 and the corresponding amino acid sequence (SEQ ID NO:8);

complete DNA sequence (SEQ ID NO:9) of the cloned cDNA of inhibitor 2 and the corresponding amino acid sequence (SEQ ID NO:10);

molecular weight of the mature recombinant protein detected by antibodies which specifically recognize the mature protein;

mature protein sequence (SEQ ID NO:11) of inhibitor-1;

mature protein sequence (SEQ ID NO:12) of inhibitor-2;

mature protein sequence (SEQ ID NO:13) of inhibitor-3

DNA coding sequence (SEQ ID NO:14) of the mature protein of inhibitor-1;

DNA coding sequence (SEQ ID NO:15) of the mature protein of inhibitor-2;

DNA coding sequence (SEQ ID NO:16) of the mature protein of inhibitor-3;

DNA coding sequence (SEQ ID NO:17) of the pre-protein of inhibitor-1;

DNA coding sequence (SEQ ID NO:18) of the pre-protein of inhibitor-2;

DNA coding sequence (SEQ ID NO:19) of the pre-protein of inhibitor-3;

In the foregoing and in the following examples, all temperatures are set forth uncorrected in degrees Celsius and unless otherwise indicated, all parts and percentages are by weight.

EXAMPLES

Example 1

Activity of the Inventive Protein

The aggregation formed by human platelets in the presence of collagen is inhibited when saliva of *Triatoma pallidipennis* or purified protein is added. The inhibition correlates with the concentration of saliva or protein.

Figure 1:
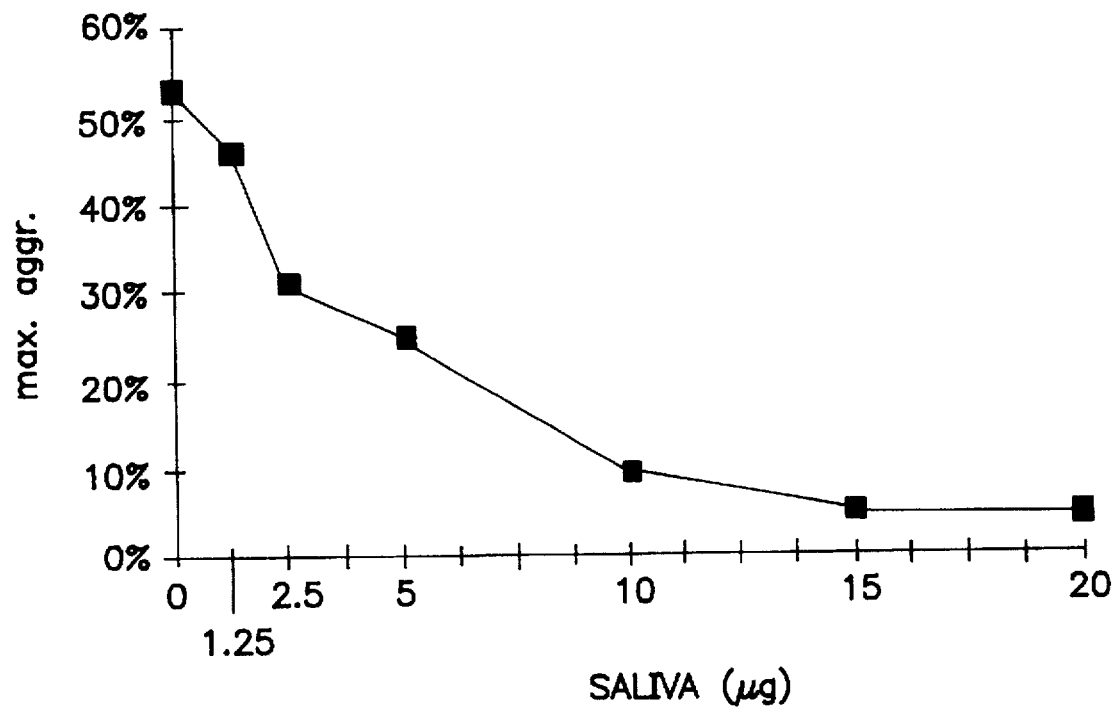
FIG. 1 shows the dose-dependent inhibition of human platelet aggregation by the saliva of Triatoma.
Figure 2:
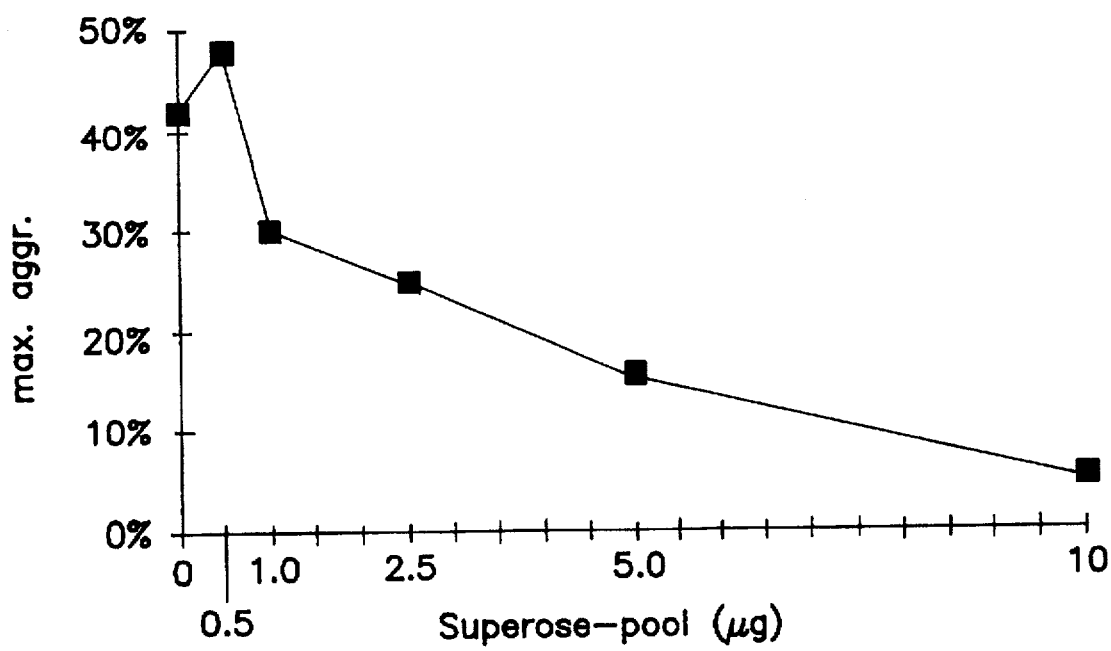
FIG. 2 shows the dose-dependent inhibition of human platelet aggregation by the "Superose"-pool of the saliva of Triatoma.

The bugs are stimulated to eject their saliva onto a siliconized glass plate by mechanical stimulation of the proboscis. The ejected material is collected using drawn-out siliconized pasteur pipettes. 500 µl platelet rich plasma (300.000 platelets/µl) is incubated with different amounts of saliva (1.25–20 µg protein in 20 µl) or with different amounts of "Superose"-pool (0.5–10 µg protein in 200 µl) from Example 2 at 37° C. in an aggregometer. After 1 min, 1 µg of collagen is added and the increase in light transmission (aggregation) is monitored. See FIGS. 1 and 2.

Example 2

Purification of the Protein

The important step to purify the protein is the use of the gel filtration using "Superose 12".

Figure 3:
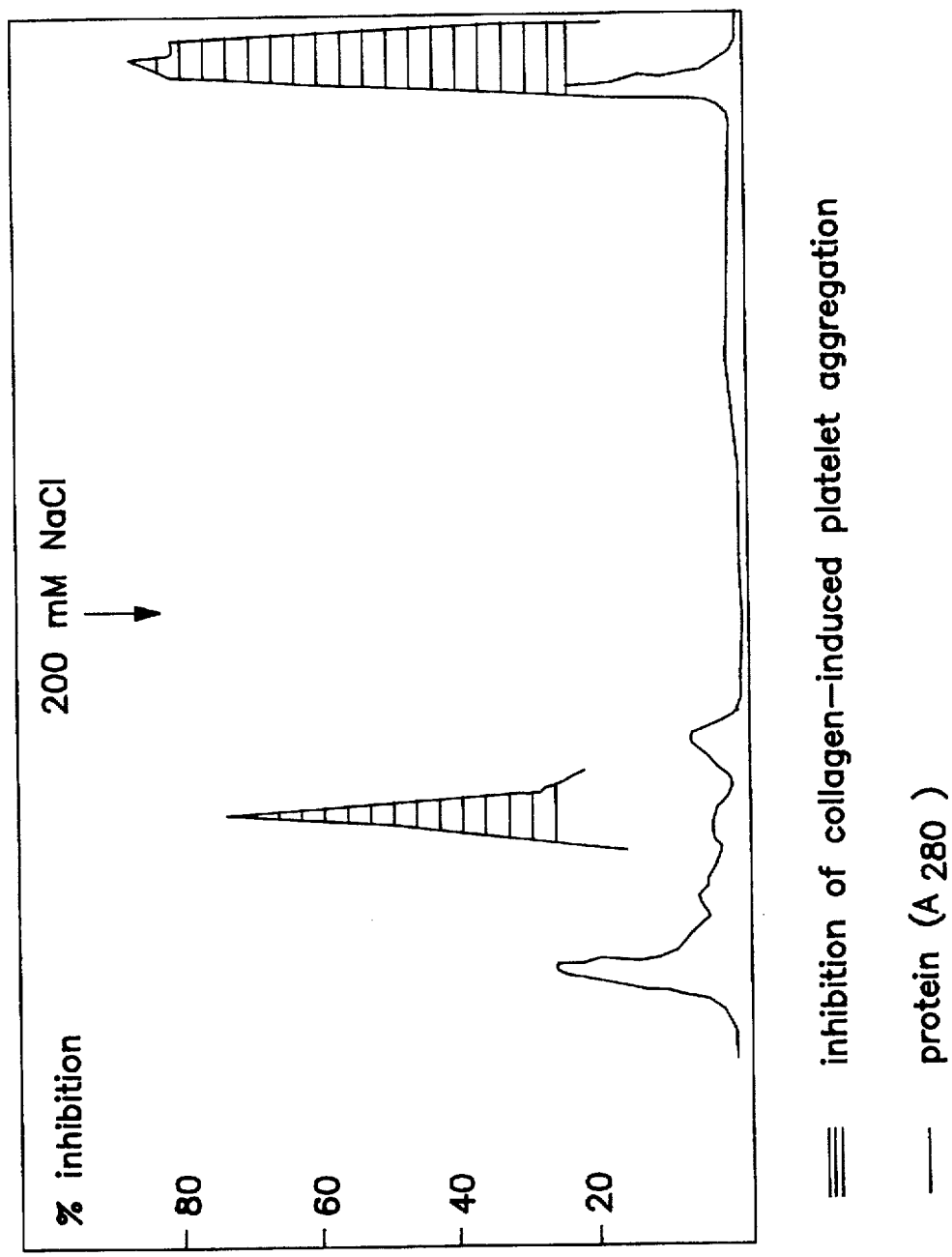
FIG. 3 shows the gel filtration pattern on "Superose 12"

2 ml (5 mg protein) of saliva is chromatographed over a "Superose 12" HR 16/50 chromatography column (Pharmacia) in 10 mM Tris/HCl, pH 7.4; 0.0001% "Pluronic F68". Thereafter, the inhibitor is eluted with 10 mM Tris/HCl, pH 7.4; 0.0001% "Pluronic F68", 200 mM NaCl. See FIG. 3. The inhibitor pool contains 25 µg/ml protein. 5 µg of protein shows a 70% inhibition of aggregation. The aggregation of platelets without inhibitor is defined as 100% aggregation and 0% inhibition. Accordingly the other data are calculated.

Example 3

The Inhibition is Independent of Fibrinogen

The inhibitory activity which is shown by the protein of the invention is independent of the concentration of added fibrinogen.

Figure 4:
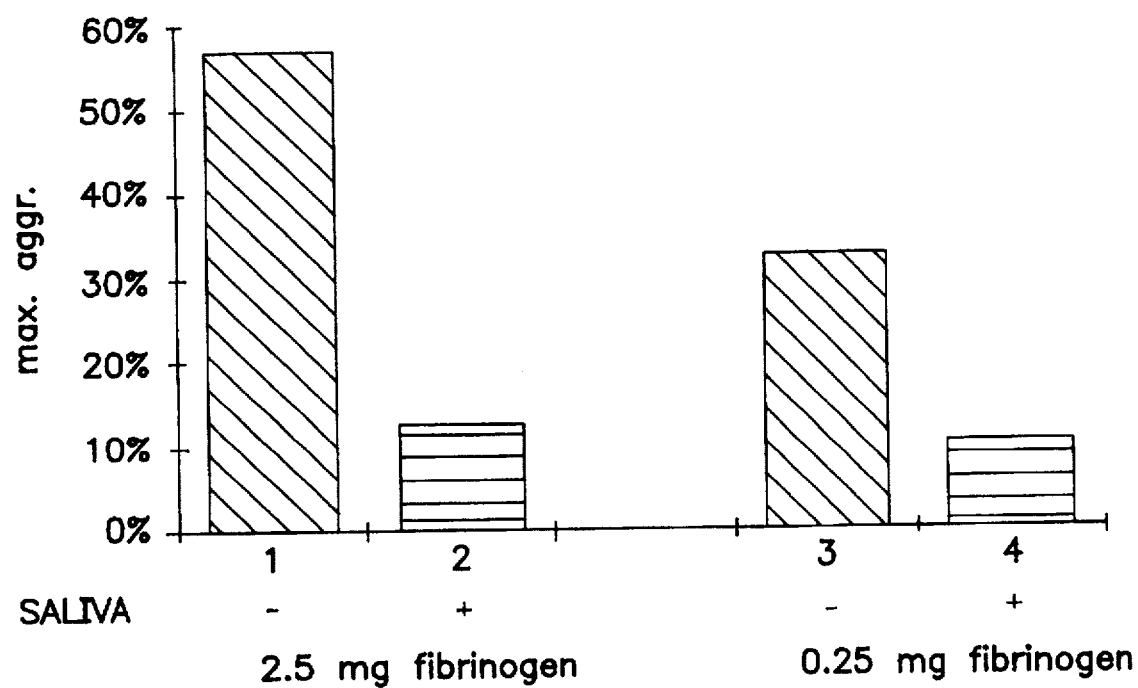
FIG. 4 shows the independence of aggregation inhibition on fibrinogen concentrations.

500 µl of gel filtrated platelets is combined with fibrinogen and 50 µg saliva. After incubation for 1 min at 37° C., 1 µg of collagen is added and the aggregation is monitored. The values represented by the bars 2 and 4 (with saliva) do not show significant differences wherein the values represented by the bars 1 and 3 (without saliva) correlate with the concentration of fibrinogen. See FIG. 4.

Example 4

Figure 5:
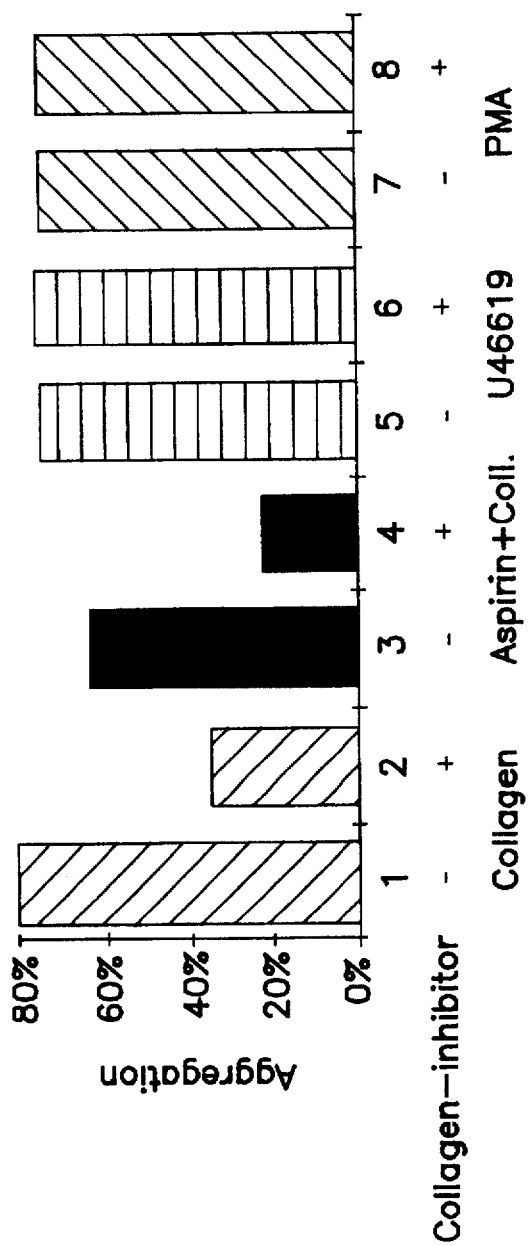
FIG. 5 shows the prevention of the collagen-induced aggregation of platelets pretreated with aspirin.

Test to Detect the Mechanism of the Platelet Aggregation Induced by the Inventive Proteins In order to study the mechanism of the protein of the invention, some standard compounds are added to a test system in which alternatively the inventive protein or buffer is present. The activity of the inventive protein is not significantly altered when the compound aspirin is added (bar 4), whereas the effect of the compounds U46619 and PMA cannot be influenced by the protein of the invention. Therefore, the protein of the invention is not a thromboxane antagonist and probably not an inhibitor of protein kinase C. Bars 1 and 2: 500 µl of platelet-rich plasma (300.000 platelets/µl) is incubated with the protein of the invention (bar 2) (200 µl "Superose"-pool) or with buffer (bar 1) respectively at 37° C. for 1 min. Then 1 µg collagen is added and the aggregation is monitored in an aggregometer. Bars 3 and 4: 500 µl of platelet-rich plasma is incubated with 1 mM of aspirin for 20 min at room temperature. Thereafter the protein of the invention (bar 4) or buffer (bar 3) is added. After an incubation period of 1 min at 37° C., 1 µg of collagen is added and the aggregation is monitored. Bars 5 and 6: 500 µl of platelet-rich plasma is incubated with the protein of the invention (bar 6) or buffer (bar 5) respectively for 1 min at 37° C. Then U46619 (1 µM) is added and the aggregation is monitored. Bars 7 and 8: 500 µl of platelet-rich plasma is incubated with the protein of the invention (bar 8) or buffer (7) respectively at 37° C. in an aggregometer. After 1 min, 10 ng of PMA (phorbol-12-myristate-13-acetate) is added and the aggregation is monitored. Results are shown in FIG. 5.

Example 5

Platelet-release Reaction (ATP Measurement)

When platelets and collagen are present, the protein of the invention can inhibit the activation of the platelets.

ATP is used as an indicator for activation. 500 µl of platelet-rich-plasma is incubated with 200 µl of protein of the invention (Superose-pool) or $H_2O$ respectively at 37° C. for 1 min. Then 1 µg of collagen is added.

The aggregation is monitored for 10 min. Thereafter, 200 µl of the suspension is combined with 250 µl Hepes buffer pH 7.4, 100 mM luciferin and 5 μg/ml luciferase. Then the luminescence is measured.

The total ATP content of the platelets is determined after lysis of the platelets with "Nonidet P40".

| amount of inventive protein added | max. aggr. | released ATP % of total ATP content |
|---|---|---|
| — | 68% | 49% |
| 15 μl (=5 μg protein) | 49% | 15% |
| 30 μl (=10 μg protein) | 18% | 2% |

Example 6

Inhibition of Platelet Aggregation Induced by Different Substances

The protein of the invention is specific for collagen-induced platelet aggregation. 500 μl of filtrated platelets (300,000 platelets/μl) are incubated with the protein of the invention for 1 min at 37° C. Then the aggregation is induced with collagen (2 μg/ml), thrombin (0.06 U/ml) or ADP (1–10$^{-5}$ M) respectively and the aggregation is monitored.

| | maximal aggregation | | |
|---|---|---|---|
| | collagen | thrombin | ADP |
| control | 64% | 75% | 57% |
| partially purified protein (200 μl) "Superose"-pool | 23% | 75% | 44% |

Example 7

Inhibition of Collagen-Induced Aggregation

The protein of the invention does not react with collagen.

Figure 6:
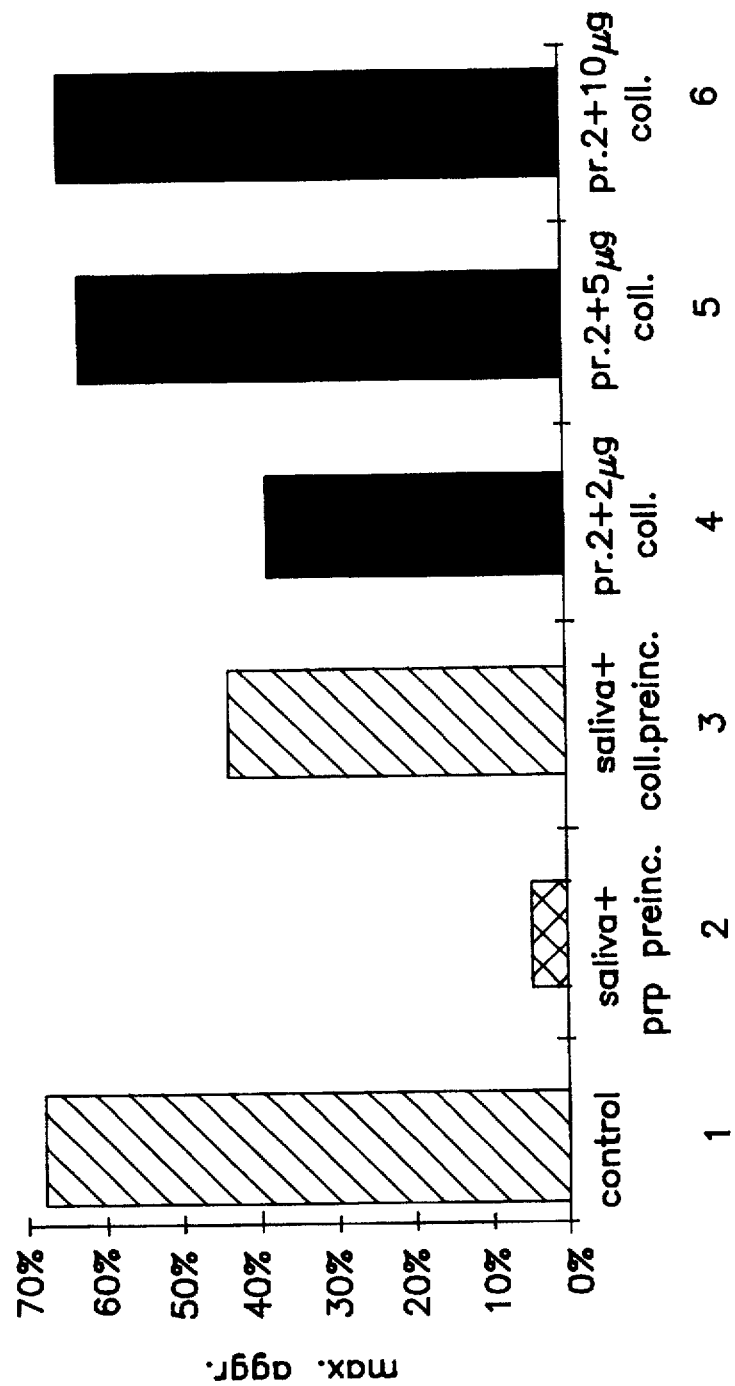
FIG. 6 shows no reaction of the inhibitor with collagen.

The inhibition of collagen-induced platelet aggregation in presence of the protein can be neutralized by a surplus of additionally added collagen. The collagen-induced aggregation (2 μg/ml) of 500 μl of platelet-rich plasma is measured with the following modifications:
1: control, without inhibitor;
2: protein of the invention (100 μg of saliva) 10 min preincubated with human platelets prior to addition of collagen;
3: inhibitor (100 μg of saliva) 10 min preincubated with collagen prior addition of platelet-rich-plasma
4, 5, 6: after measurement of the aggregation, 2, 5 and 10 μg of collagen, respectively, is added to probe No. 2 and aggregation is measured again.
See FIG. 6.

Example 8

Impact of Protease Inhibitors on the Inhibitory Activity

The protein of the invention is not a protease.

Protease inhibitors (2 mM PMSF, 2 mM leupeptin, 2 mM aprotenin) or buffers are incubated for 15 min with the "Superose"-pool (200 μl). Then platelet-rich-plasma is added and the aggregation is started with collagen (2 μg/ml).

| | maximal aggregation |
|---|---|
| control (without inventive protein) | 86% |
| +"Superose"-pool | 52% |
| +"Superose"-pool + protease inhibitors | 48% |

Example 9

The Inhibition is Dependent on the Presence of Mg$^{2+}$

The cation Mg$^{2+}$ increases the inhibition of platelet aggregation by the protein of the invention. Wherein the cation Ca$^{2+}$ has no significant influence on the inhibition of the platelet aggregation. 500 μl of platelet-rich plasma is combined with 2 mM Mg$^{2+}$ or Ca$^{2+}$ and 40 μg saliva or buffer. After incubation for 1 min at 37° C., 1 μg of collagen is added and the aggregation is monitored.

| Additives | maximal aggregation |
|---|---|
| — | 77% |
| saliva | 33% |
| 2 mM Mg$^{2+}$ | 75% |
| saliva + 2 mM Mg$^{2+}$ | 19% |
| 2 mM Ca$^{2+}$ | 63% |
| saliva + 2 mM Ca$^{2+}$ | 39% |

Example 10

Platelets Incubated With the Protein of the Invention Show Decreased Adhesion to Collagen When platelets are incubated with the inventive protein, they partially loose their capability to bind collagen.

A 96 well plate is coated with collagen (type I at 4° C. overnight). 1–10$^7$ platelets per well are incubated with different amounts of inhibitor and 2 mM Mg$^{2+}$ for 20 min at 37° C. with agitation. They are washed with PBS and the adherent platelets are fixed with 2.5% glutardialdehyde for 2 h at 37° C. Then the platelets are removed from the well and counted under a microscope.

| protein* | adherent platelets per mm$^2$ |
|---|---|
| — | 13500 |
| 10 μl | 12000 |
| 50 μl | 6500 |

*protein = "Superose"-pool concentrated to 0.5 mg protein/ml

Example 11

Incubation of the Inhibitor with Trypsin-Sepharose

The protein of the invention is digested by trypsin bound to Sepharose. The digestion of the inventive protein results in a complete loss of the activity of the inventive protein.

Figure 7:
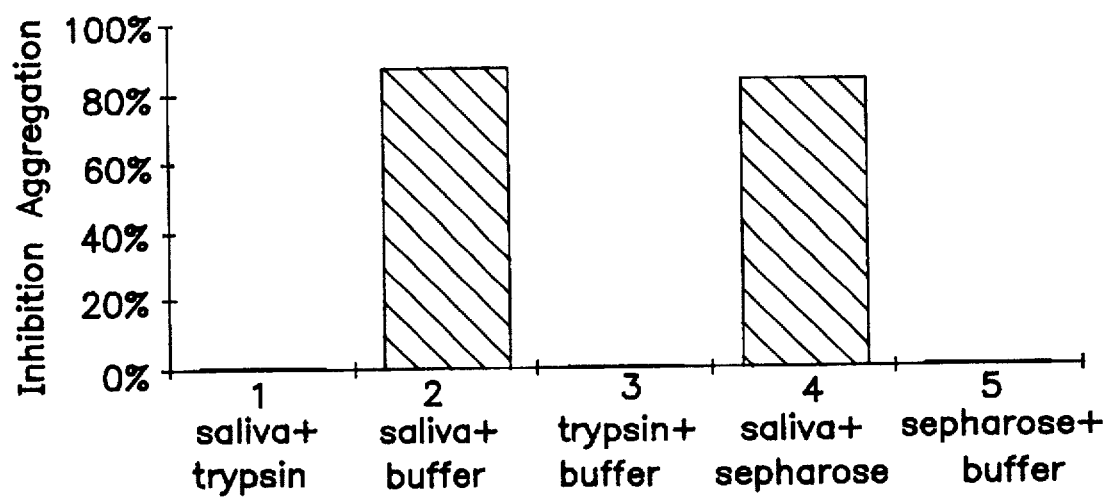
FIG. 7 shows the proteolytic digestion of the inhibitor.

200 μg of saliva is combined with trypsin bound to Sepharose or with buffer or with Sepharose respectively and trypsin-Sepharose is combined with buffer. All batches contain 150 mM of NaCl to prevent nonspecific adsorption to the matrix. After incubation overnight at room temperature with agitation, the batches are centrifuged and the supernatants are added to an aggregation assay (500 μl of platelet-rich-plasma, 1 μg of collagen). The proteolytic digestion is monitored on a SDS-polyacrylamide gel. See FIG. 7.

Example 12

Incubation of the Inhibitor with Collagenase-Sepharose

The protein of the invention is not cleavable by a collagenase.

Collagenase (*Clostridium histolyticum*) is bound to Sepharose and used in the following batches:

1. 100 µl of collagenase-Sepharose+60 µl of protein of the invention +140 µl of H₂O+10 µl buffer.
2. 100 µl of 150 mM NaCl, 50 mM Tris/HCl pH 7.4+60 µl of protein of the invention+140 µl of H₂O+10 µl of buffer.
3. 100 µl of collagenase-Sepharose+200 µl of H₂O+10 µl of buffer.

As a control, bovine serum albumin is coupled to Sepharose and is used in the following batches:

4. 100 µl of BSA-Sepharose+60 µl of protein of the invention+140 µl of H₂O+10 µl of buffer.
5. 100 µl of BSA-Sepharose+200 µl of H₂O+10 µl of buffer. protein: "Superose"-pool buffer: 140 mM Tris/HCl, pH 7.4, 100 mM CaCl₂.

Figure 8:
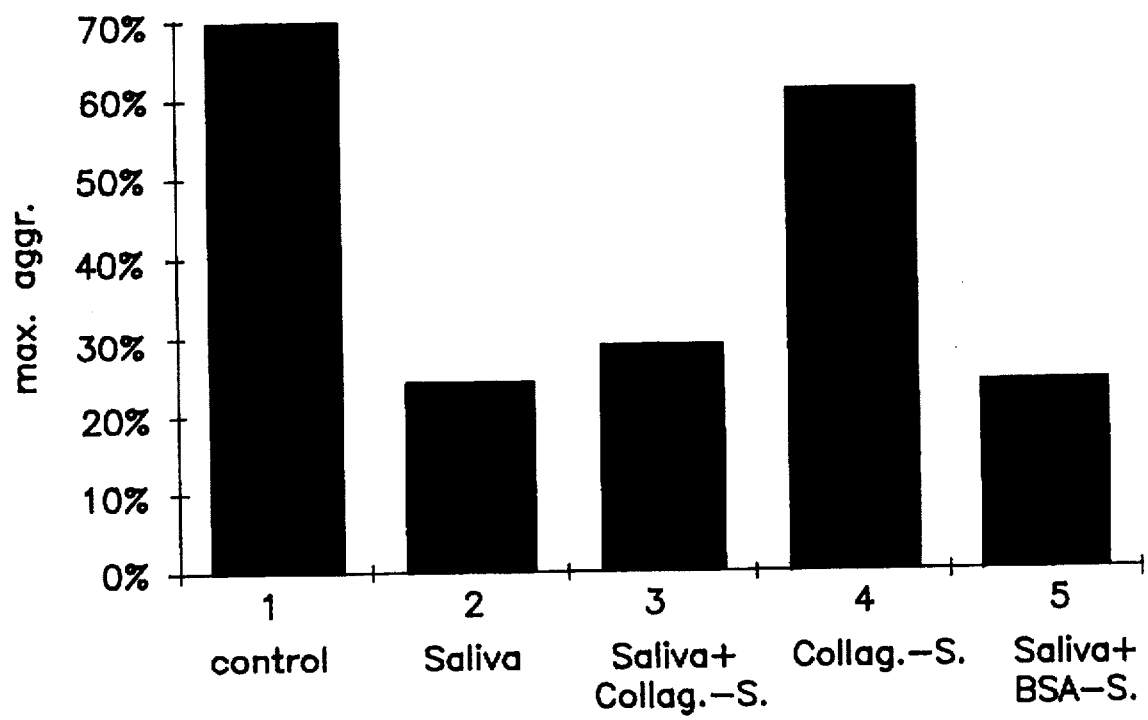
FIG. 8 shows the stability of the inhibitor against collagenase.

The batches are centrifuged and 200 µl of each supernatant is incubated with 500 µl of platelet-rich plasma for 1 min at 37° C. Then 1 µg collagen is added and the aggregation is monitored. The activity of the collagenase-Sepharose is monitored by incubating it with collagen and running a SDS-polyacrylamide gel electrophoresis. See FIG. 8.

Example 13

Molecular Mass Determination for the Inhibitor by Gel Filtration

The purified protein of the invention shows a molecular weight of 20,000±5,000 Dalton measured by a Superose 12 column filtration.

Figure 9:
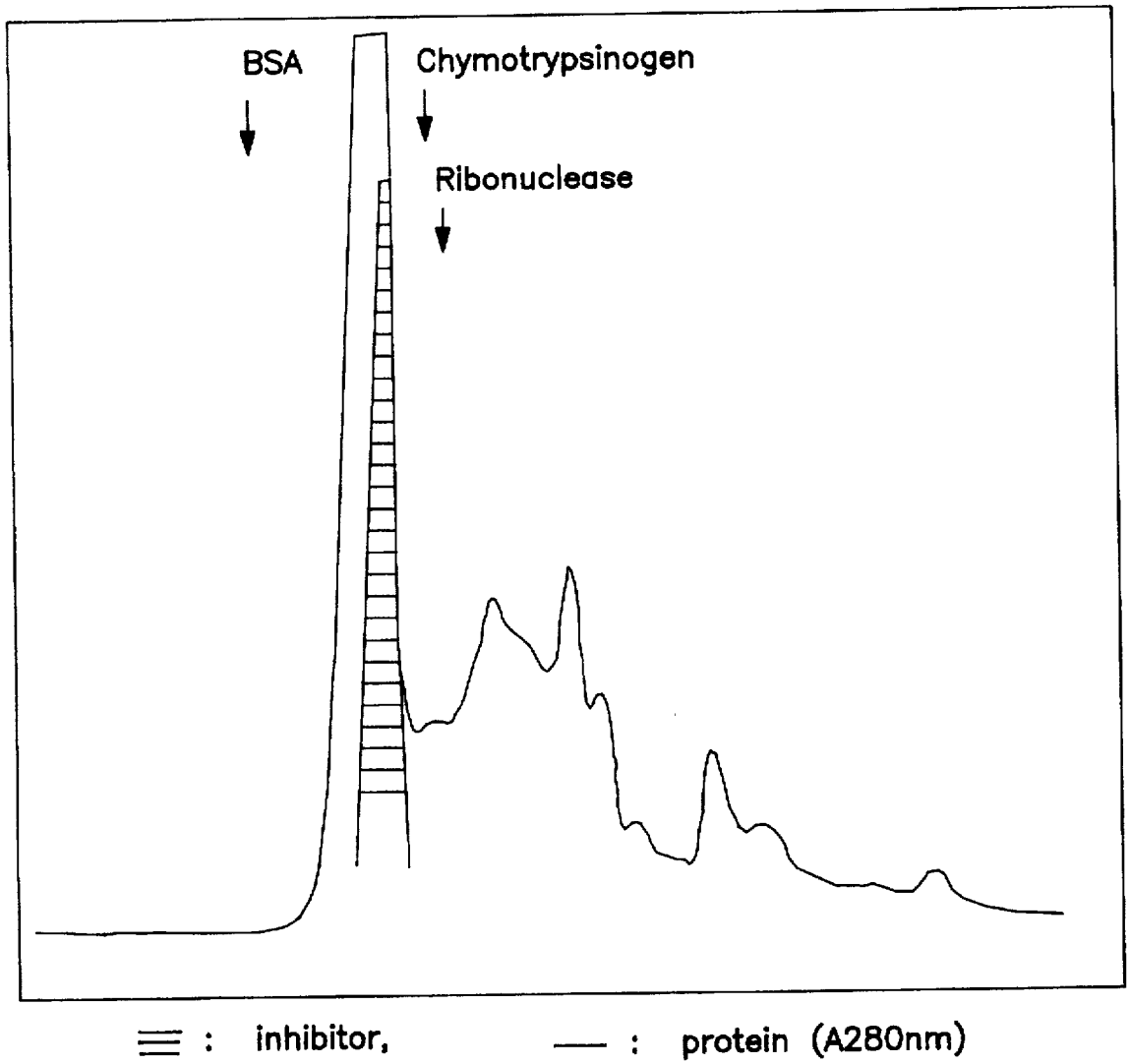
FIG. 9 shows the determination of the molecular weight of the inhibitor.

The "Superose"-pool from 2 ml of saliva (see Example 2) is chromatographed over a "Superose 12" HR16/50 column in Tris/HCl pH 7.4, 150 mM NaCl, 0.0001% "Pluronic" F68. Bovine serum albumin (MW 67 kDa), chymotrypsinogen (MW 25 kDa) ribonuclease (MW 14 kDa) are used as molecular weight makers. See FIG. 9.

Example 14

The Adhesion of Tumor Cells to Collagen is Decreased in the Presence of the Protein of the Invention The protein of the invention inhibits the adhesion of tumor cells to a collagen matrix. Therefore, migrating tumor cells can be prevent partially or completely from settling down in organs or blood vessels, when the protein of the invention is within the blood or the plasma of the patient.

MTLn3 cells (rat mammary tumor cells) are labelled with ⁵¹Cr. A well plate is coated with collagen (type III) at 4° C. overnight. 2–10⁴ labelled cells in 500 µl DMEM F12 medium, 20 mM Hepes, 1 mM bicarbonate, 1% BSA are first incubated with 0, 2, 5 or 10 µl protein of the invention ("Superose Pool", 0.5 mg protein/ml) respectively for 10 min at 37° C. Then this suspension is transferred to a collagen-coated well and incubated for 2 h at 37° C. Thereafter, the wells are washed and the adherent cells are removed with 1M NaOH. The radioactivity of the adherent cells are counted.

| amount of the inhibitor added µl | cell attachment (cpm) |
| --- | --- |
| 0 | 2215 |
| 2 | 2071 |
| 5 | 1608 |
| 10 | 1081 |

Example 15

Purification of the Inhibitor to Homogeneity

The protein of the invention isolated according Example 2 is purified to homogeneity by using a High Performance Electrophoresis Chromatography System.

Figure 10:
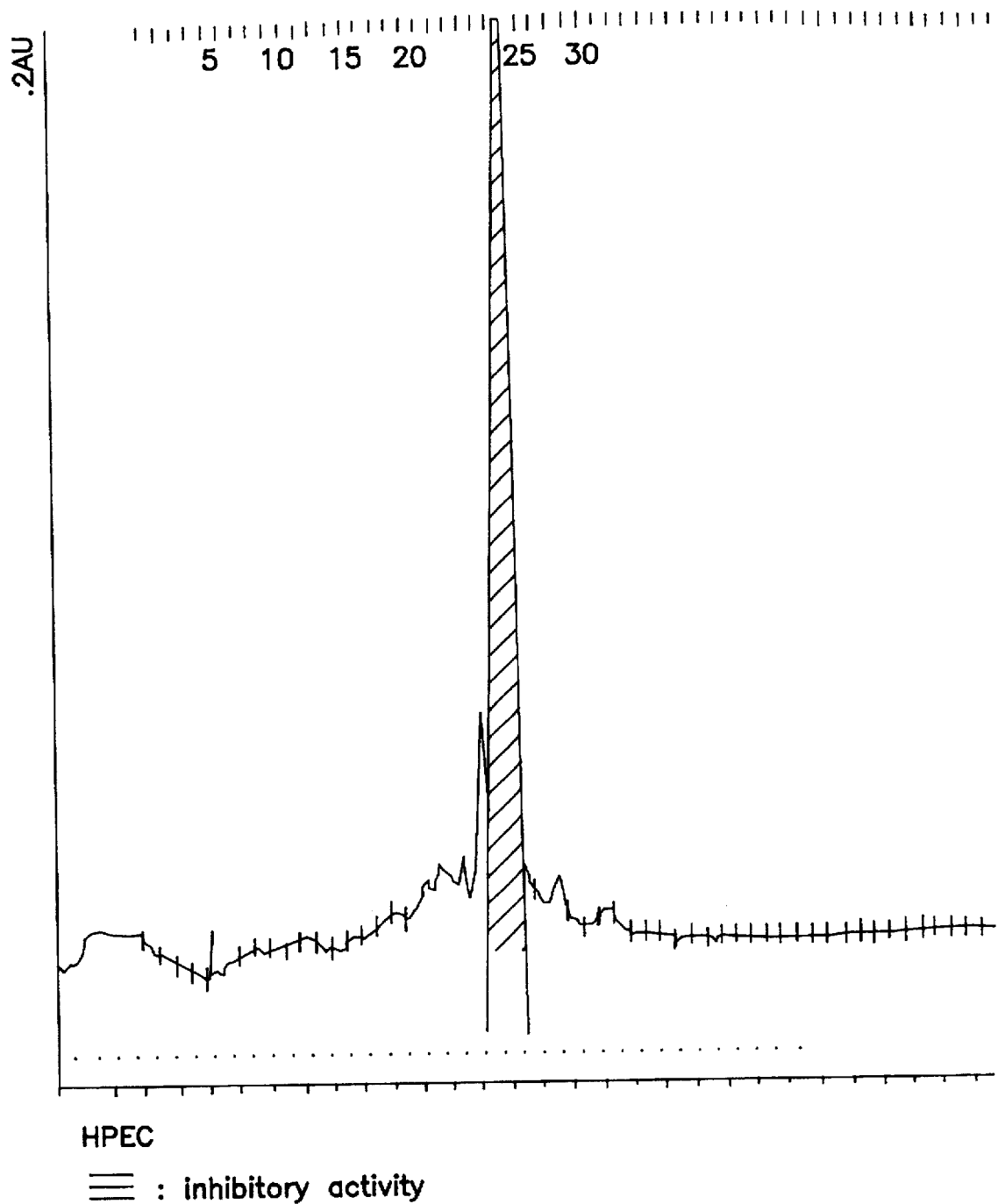
FIG. 10 shows the purification of the inhibitor to homogeneity.

The partially purified inhibitor is applied to a High Performance Electrophoresis Chromatography System (HPEC) from Applied Biosystems, Inc. (Foster City, Calif.). The electrophoresis is performed on a 7.5% polyacrylamide-gel in a Tris/glycine buffer system according to the manufacturer's instructions. The sample buffer contained SDS but no reducing agent (e.g., DTT) and the aliquot is not heated prior to being loaded onto the gel. The protein is successively eluted from the gel, detected by measuring the absorption at 230 nm and fractionated. Fractions which have inhibitory activity are analyzed by a SDS-polyacrylamide-gel-electrophoresis (12.5% SDS-polyacrylamidegel, stained with Coomassie Brilliant Blue). See FIG. 10.

Example 16

Amino Acid Analysis

Protein samples are evaporated to dryness and hydrolyzed in 6N HCl containing 2% phenol, for 24, 48 and 72 hours. Cysteine content is determined as cysteic acid after performic acid oxidation (Moore, J. Biol. Chem. 238, 235–27 (1963)). Tryptophan is measured after hydrolysis in 4N N-methanesulfonic-acid for 24 hours (Simpson et al., J. Biol. Chem. 251, 1936–1940 (1976)). The samples are then analyzed on an amino acid analyzer. The analysis shows the following results (indicated in % of all amino acids): Gly= 8.3%; Ala=1.6%; Ser=8.9%; Thr=10.7%; Val=8.7%; Leu= 6.6%; Ile=2.5%; Pro=4.5%; Cys=3.0%; Met=1.0%; His= 2.3%; Tyr=4.3%; Asp=6.2%; Glu=7.2%; Lys=11.0%; Arg= 1.8%; Asn=5.7%; Gln=2.3%; Phe=2.5%; and Trp =1.1%.

Example 17

Amino Acid Sequencing

The protein is sequenced on an Applied Biosystems, Inc. (ABI) (Foster City, Calif.) Automatic Amino Acid Sequenator according to the manufacturer's instructions. The sequence of amino acids 1–20 (from the N-terminus) is:

Glu-Glu-Cys-Glu-Leu-Met-Pro-Pro-Gly-Asp-Asp-Phe-Asp-Leu-Glu-Lys-
1           5           10          15

Tyr-Phe-Ser-Ile (Amino Acids 1–20 of SEQ ID NO: 11)
17  18    20

Example 18

Figure 12:
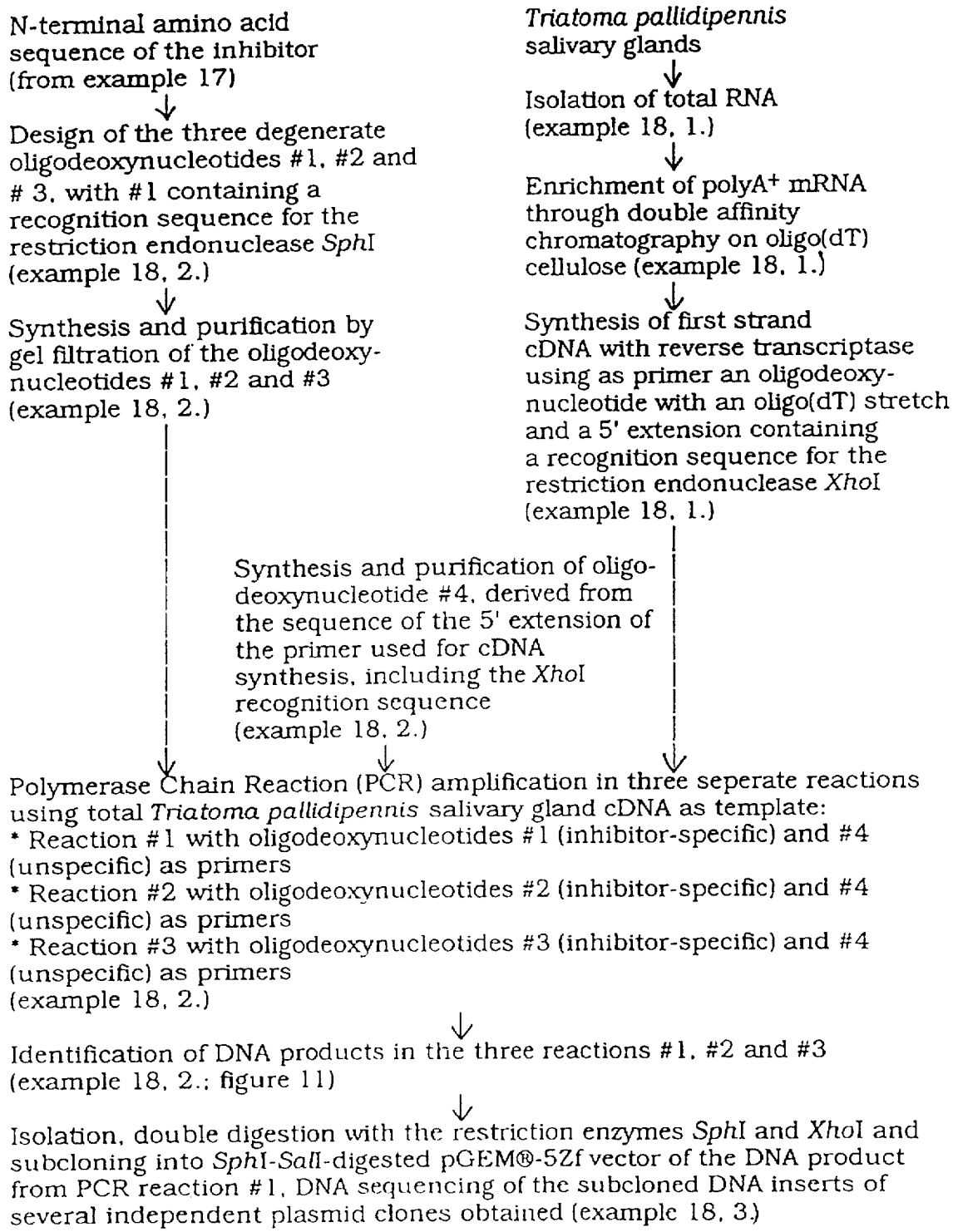
FIG. 12 shows the flow diagram of finding the cDNA of the invention.

PCR Amplification, Subcloning and DNA Sequencing of Major Fragments of Three Forms of Inhibitor cDNA from *Triatoma pallidipennis* Salivary Gland cDNA Part 1. Preparation of *Triatoma pallidipennis* salivary gland RNA and synthesis of first strand cDNA Starting with the total purified RNA from the salivary glands, the sequences of the RNA are transcribed by the reverse transcriptase to contain first strand cDNAs. A special oligodeoxynucleotide is used for priming of first strand cDNA synthesis. Total RNA is isolated from the salivary glands of *Triatoma pallidipennis* in a procedure involving the dissolution of tissue in guanidinium thiocyanate and subsequent ultra-centrifugation of the lysate on a cesium chloride cushion (Sambrook, J., Fritsch, E. F., Maniatis, T.: Molecular Cloning, Chapter 7, 18–22, Cold Spring Harbor Laboratory Press, 1989). 10 μg of total salivary gland RNA thus obtained are used to synthesize the first strand of complementary DNA (cDNA). For this purpose, Moloney Murine Leukemia Virus reverse transcriptase, the corresponding reaction buffer, deoxynucleotides and RNase block II from a commercially available "1st Strand Synthesis Kit" (Stratagene Cloning Systems, La Jolla, Calif., U.S.A.) are used as described in the manufacturer's protocol. The oligodeoxynucleotide incorporated in the annealing step of the reaction for priming first strand cDNA synthesis is not one of those included in the "1st Strand Synthesis Kit" but is a linker-primer (input: 1.4 μg) taken from the commercially available "ZAP-cDNA™ Synthesis Kit" (Stratagene Cloning Systems). Its sequence is a s follows (an XhoI restriction endonuclease recognition sequence is underlined; see also the summary in FIG. 12)

The oligodeoxynucleotides correspond to different partially overlapping parts of the found amino acid sequence by Edman degradation. Oligodeoxynucleotide #3 comprises the oligodeoxynucleotide #1 in the beginning and the oligodeoxynucleotide #2 in the end.

An additional oligodeoxynucleotide is made with a sequence derived from the linker-primer used for the priming of first strand cDNA synthesis (see Part 1.):

Oligodeoxynucleotide #4:

5'-GAGAGAGAGAACTAG<u>TCTCGAG</u>-3' (SEQ ID NO: 28)
<div style="text-align:center">XhoI</div>

After synthesis on an Applied Biosystems PCR-Mate™ 391 DNA synthesizer, the four oligodeoxynucleotides are purified through gel filtration on commercially available NAP-5 columns (Pharmacia Biosystems) and used as primers in three separate polymerase chain reactions (PCR; U.S. Pat. No. 4,800,159) as described below. Reagents from a commercially available "GeneAmp™ DNA Amplification Kit" with AmpliTaq™ recombinant Taq DNA polymerase from Perkin-Elmer Cetus (Norwalk, Conn., U.S.A.) are used according to the supplier's protocol. 5% (2.5 μl) of the total amount of the first strand cDNA synthesized from Triatoma salivary gland total RNA (see Part 1.) serves as template in each of the three PCR reactions. The oligodeoxynucleotide 5'-GAGAGAGAGAGAGAGAGAGAACTAG<u>TCTCGAG</u>TTTTTTTTTTTTTTTTTTT-3' (SEQ ID NO: 21)
<div style="text-align:center">XhoI</div>

Part 2. PCR amplification of inhibitor cDNA fragments from the salivary gland first strand CDNA Taking the amino acid sequence, which is determined by Edman degradation of the purified protein of the invention, three oligodeoxynucleotides and one linker oligodeoxynucleotide are devised and synthesized. Based on selected stretches of the amino acid sequence determined for the N-terminus of purified inhibitor (Example 17), three degenerated oligodeoxynucleotides are devised and synthesized for the amplification of a major part of inhibitor cDNA. Their sequences are as follows ("I" stands for deoxyinosine, two letters in parentheses divided by a slash indicate positions where two different deoxynucleotides are incorporated, the corresponding amino acid sequence is indicated in three-letter code under the deoxynucleotide sequence, an SphI restriction endonuclease recognition sequence is underlined):

primers are combined in the following way: oligodeoxynucleotides #1 and #4 in PCR reaction #1, oligodeoxynucleotides #2 and #4 in PCR reaction #2, oligodeoxynucleotides #3 and #4 in PCR reaction #3. The three PCR reactions are incubated in a Perkin Elmer Cetus Thermal DNA Cycler using the following cycling program with 38 cycles comprising cycling steps #1 through #3:

*initial step: 3 min at 94° C.
 *cycling program:
 *cycling step #1: 1 min 30 sec at 94° C.
 *cycling step #2: 2 min at 40° C.
 *cycling step #3: 3 min at 72° C.
 (The sequence of cycling steps #1 through #3 is repeated 38 times.)
 *final step: 10 min at 72° C.

5% (5 μl) of the total reaction volumes are separated by electrophoresis on a 1.5% agarose gel using a 123 base-pair ladder DNA size standard (Gibco-BRL Life Technologies, Oligodeoxynucleotide #1:
5'-GC<u>GGC ATG</u> CCI CCI GGI GA(C/T) AA(C/T) TT(C/T) GA-3' (SEQ ID NO: 2)
    <u>SphI</u>
    Met Pro Pro Gly Asp Asn Phe Asp Oligodeoxynucleotide #2: (SEQ ID NO: 23)
5'-AAC TTT GA(C/T) (C/T)TI GA(G/A) AA(G/A) TA(C/T) TT-3' (SEQ ID NO: 24)
   Asn Phe Asp Leu Glu Lys Tyr Phe (SEQ ID NO: 25)

Oligodeoxynucleotide #3:
5'-ATG CCI CCI GGI GA(C/T) AA(C/T) TTT GA(C/T) (C/T)TI GAG AAG
   Met Pro Pro Gly Asp Asn Phe Asp Leu Glu Lys cont.
    TA(C/T) TT-3' (SEQ ID NO: 26)
    Tyr Phe (SEQ ID NO:27)

Gaithersburg, Md., U.S.A.). After staining of the gel with ethidium bromide, single DNA bands are found for each of the three PCR reactions, their apparent sizes according to the DNA size standard being approximately 530 to 560 base pairs.

Part 3. Subcloning and sequencing of the inhibitor cDNA fragments

The DNA fragment contained in the remaining volume of PCR reaction #1 (see 2.) is isolated after electrophoresis on a 1.5% agarose gel in a procedure involving binding to and elution of the DNA from NA-45 DEAE membrane (Schleicher & Schuell, D-3354 Dassel, Germany), followed by extraction with n-butanol and ethanol precipitation (Sambrook, J., Fritsch, E. F., Maniatis, T.: Molecular Cloning, Chapter 6, 24–27, Cold Spring Harbor Laboratory Press, 1989). The ends of the recovered DNA fragment are made suitable for ligation to a vector by double digestion with the restriction enzymes SphI and XhoI (Boehringer Mannheim GmbH, D-6800 Mannheim, Germany) and then extracted twice with phenol/chloroform (1:1) and subsequently twice with chloroform. 3 µg of DNA of the plasmid vector pGEM$^R$-5Zf(−) (Promega, Madison, Wis., U.S.A.) are linearized through a double digestion using the restriction enzymes SphI and SalI (Boehringer Mannheim GmbH) and then separated on and isolated from a 1.5% agarose gel as described above. 50% of the digested and extracted amplified DNA fragment and 20% of the digested and gel-purified vector DNA are combined, ethanol precipitated and ligated using the reagents and the protocol of a commercially available "DNA Ligation Kit" (Stratagene Cloning Systems). The entire ligation reaction is used for transformation of commercially available "Epicurian Coli® XL1-Blue Supercompetent Cells" (Stratagene Cloning Systems) according to the supplier's protocol. The entire transformation reaction is plated on LB agar plates containing ampicillin (100 µg/ml). 20 of the ampicillin-resistant E. coli cell clones found after incubation are propagated in LB broth containing ampicillin (100 µg/ml) and their plasmid DNA is isolated in an alkaline lysis "miniprep" procedure (Sambrook, J., Fritsch, E. F. Maniatis, T.: Molecular Cloning, Chapter 1, 25–28, Cold Spring Harbor Laboratory Press, 1989). After double digestion of the plasmid DNA from the 20 clones with the restriction endonucleases SphI and SacI (Boehringer Mannheim GmbH) and electrophoresis on a 1.5% agarose gel, 13 of them are found to carry a DNA insert of an apparent size of approximately 580 bp ("positive clones"). DNA sequencing is performed on the phenol/chloroform-extracted plasmid DNA of 5 of theses positive clones using a commercially available "Sequenase® Version 2.0 DNA Sequencing Kit" (United States Biochemical Corporation, Cleveland, Ohio, U.S.A.) after priming with both T7 or SP6 primers (Promega). The complete insert sequences of the different plasmids is determined in this way. A single open reading frame can be identified in each of the five insert sequences. Three types of insert sequences are found with respect to the amino acid sequences derived from the open reading frame, three of the sequenced plasmid clones belonging to the type #1 and one each to the type #2 and type #3 of the derived amino acid sequence. The complete DNA insert sequences of one representative of each of the three plasmid types #1 through #3 are depicted in SEQ ID NOS:1–6 together with the amino acid sequence translated from the open reading frame. The sequence of the first 15 amino acids derived from each type of plasmid insert is identical to that determined for amino acid position 6 to 20 of the N-terminus of the inhibitor isolated from Triatoma saliva (Example 17).

Example 19

Locating, Isolating and Cloning a Gene Coding for a Platelet Aggregation Inhibitor A genomic library containing cloned restriction fragments from a restriction endonuclease digests of T. pallidipennis DNA is screened with the probes on replicate filter lifts according to standard methods. Clones which hybridize with the probe are selected. The DNA insert from these clones is then further subcloned according to standard methods until a minimum-sized DNA is isolated which binds to the probe.

These fragments are sequenced and then transferred into a suitable eukaryotic expression vector by inserting the coding region into an expression vector containing all of the elements required for expression, e.g., a promoter sequence, a terminator sequence and an origin of replication, all of which are operably linked to the PAI gene (PAI=platelet aggregation inhibitor), as well as a selection marker for isolating the thus-formed expression vector. The expression vector is then transformed into the eukaryotic host for which it is designed, and the PAI expression product is isolated.

Example 20

Sequencing the Gene Coding for Platelet Aggregation Inhibitor (PAI)

Single- and double-stranded DNA sequencing is carried out using the dideoxynucleotide chain termination method as described in Sanger et al., Proc. Natl. Acad. Sci. U.S.A. (1977) 74, 5463–5467.

Example 21

Screening Genomic Libraries and Mutant Clones for New Sequences Related to the T. pallidipennis Sequence As above, the probes derived from the amino acid sequence of the inhibitor isolated from T. pallidipennis are used to screen other genomic libraries for sequences related to the present inhibitor. Similarly, libraries of mutant inhibitors, produced by routine mutagenesis of vectors containing the gene for the T. pallidipennis inhibitor as produced above with NNMG and by site directed mutagenesis, are screened for activity.

Example 22

Isolation, Characterization and Sequencing of Complete cDNA Clones for Two Proteins of Invention as Isoforms a) General Approach A cDNA library derived from polyA(+) RNA extracted from T. pallidipennis is screened with the probe of Example 18 on replicate filter lifts according to standard methods. Positive clones are purified by separate plating out and repetition of the plaque filter hybridization. The cDNA of the longest cDNA clones are sequenced by the dideoxynucleotide method of Sanger.

b) Concrete description of the assays

Part 1. Construction of a cDNA library from Triatoma pallidipennis salivary gland RNA Approximately 500 µg of total RNA isolated from Triatoma pallidipennis salivary glands as described above (Example 18, Part 1.) are used for the isolation of polyA(+) mRNA through double affinity chromatography on oligo (dT)-cellulose. For this purpose, a commercial available "mRNA Purification Kit" (Pharmacia Biosystems GmbH, W-7800 Freiburg, Germany) is used for two subsequent rounds of enrichment as described in the manufacturer's instructions. The final yield after the second purification step is 13 µg of polyA(+) mRNA. 5 µg of this preparation is used for the construction of a cDNA library in the "Lambda ZAP® II" bacteriophage vector with the reagents and procedures of the commercially available "ZAP-cDNA™ Gigapack® II Gold Cloning Kit" (Stratagene Cloning Systems). 33% of the final yield of the first cDNA fraction after size-fractioning are ligated to 2 µg of the bacteriophage vector DNA. After packaging of the entire ligation reaction in 7 separate packaging reactions, an unamplified cDNA library with a total of 20×10⁶ independent recombinant phages is obtained.

Part 2. Isolation of the inhibitor cDNA clones from the *Triatoma pallidipennis* salivary cDNA library A total of 5×10⁵ recombinant phages from the cDNA library described above (1.) are screened through DNA-DNA hybridization of double plaque lifts on Biodyne® A nylon membranes (Pall BioSupport, East Hills, N.Y., U.S.A.). Hybridization is carried out in a solution containing 5× SSC, 5 × Denhardt's solution, 0.2% SDS and 100 µg/ml of denatured phenol-extracted sonicated salmon sperm DNA (Sigma Chemical Company, St. Louis, Mo., U.S.A.) with a radiolabeled DNA probe prepared as described below. The insert DNA of a plasmid clone of type #1 from Example 18 is isolated after double digestion using the restriction endonucleases SphI and SacI as described above. Approximately 25 ng of the recovered insert DNA are radiolabeled using a "Prime-IT™ Random Primer Labeling Kit" (Stratagene Cloning Systems) in the presence of [α-³²P] dCTP (3000 Ci/mmol; Amersham Buchler, W-3300 Braunschweig, Germany). The labeled DNA fragment is separated from unincorporated radioactivity by chromatography on a "NAP™-5" column (Pharmacia Biosystems). Filter hybridization and washing temperature is 50° C., the final wash step is in 2 × SSC with 0.2% SDS. After autoradiography at −70° C. for 48 hours, more than 300 plaques are found to yield signals on both replica filters. The bacteriophages from 80 areas around such positive signals are eluted from the original overlay plate and replated separately, at a density allowing for the purification of single phage clones. The plaque hybridization procedure described above is repeated using the same DNA probe and a total of 76 independent phage clones giving positive signals are isolated from the plates.

Part 3. Characterization and sequencing of the inhibitor cDNA clones

The phage clones are separately subjected to the "in vivo excision" procedure described in the protocol of Stratagene's cDNA library construction kit referred to above. "Miniprep" plasmid DNA from 76 different pBluescript SK plasmid clones isolated after the "in vivo excision" is cleaved in a double digestion with the restriction endonucleases EcoRI and XhoI (Boehringer Mannheim), separated on a 1.5% agarose gel and stained with ethidium bromide. A variety of different insert sizes ranging up to approximately 620 base pairs is observed. DNA sequencing with T3 and T7 primers (Stratagene Cloning Systems) is performed as described above on the plasmid DNA of 8 clones that are found to carry the largest DNA inserts of all 76 independent clones investigated. cDNA clones are thus identified that belong to 2 classes according to the amino acid sequence translated from the open reading frame, one class corresponding exactly to the type #1 plasmid insert (6 clones, called "inhibitor-1") described in example 18 (3), and the other class to the type #2 plasmid insert (2 clones, called "inhibitor-2"). Further DNA sequencing experiments are carried out to confirm the sequences established so far, using additional synthetic oligodeoxynucleotides based on the known sequences:

Oligodeoxynucleotide #5:

5'-TATCACTCTGAACTCAAGTG-3' (SEQ ID NO: 29)

Oligodeoxynucleotide #6:

5'-TTACCGCCGTTTCCATTTGG-3' (SEQ ID NO: 30)

Oligodeoxynucleotide #7:

5'-TTACTTCAAAGTTGCACC-3' (SEQ ID NO: 31)

Oligodeoxynucleotide #8:

5'-GCAACATGAAGGTGATCATTGCAGCAAC-3' (SEQ ID NO: 32)

The 5' ends of most of the longest independent clones are found to be identical, with a 5'-untranslated region of 5 base pairs, suggesting that the cDNAs of the complete mRNA transcripts including the transcription initiation point have been cloned. The complete DNA and derived amino acid sequences of the cDNA clones for inhibitor-1 and inhibitor-2 are depicted in SEQ ID NOS:7–10. The cleavage site between signal peptide and mature protein is deduced from the N-terminal amino acid sequence described in Example 17.

Example 23

Expression and Secretion of Recombinant Inhibitor in Stably Transfected Baby Hamster Kidney (BHK) Cells a) General approach The coding sequence from the cDNA clones is then transferred into a suitable eukaryotic expression vector by inserting the coding region into an expression vector containing all of the elements required for expression, e.g., a promoter sequence, a terminator sequence and an origin of replication, all of which are operably linked to the PAI gene, as well as a selection marker for isolating the thus-formed expression vector. The expression vector is then transformed into the eukaryotic host for which it is designed, and the PAI expression product is isolated.

b) Concrete description of the assays

Part 1. Construction of expression plasmids for the inhibitor using the pMPSV/CMV vector Two oligodeoxynucleotides are synthesized for the PCR amplification of inhibitor-coding sequences from both inhibitor-1 and inhibitor-2 plasmid cDNA clones. One of them (#9) is deduced from the coding strand of the region around the ATG initiation codon, prolonged with a 5' tail including a HindIII recognition sequence and an optimized "Kozak site" (Kozak, M.: Point mutations define a sequence flanking the AUG initiation codon that modulates translation by eukaryotic ribosomes. Cell 44, 283–292, 1986), while the other (#10) is deduced from the non-coding strand of the region around the TAA termination codon of the open reading frames, prolonged with a 5' tail including a HindIII recognition sequence (recognition sequences of the restriction endonuclease HindIII are underlined, the optimized "Kozak site" for efficient translation initiation is indicated with asterisks, the portions of the sequences matching one or the other strand of the original cDNA clone sequences are in italics):

Oligodeoxynucleotide #9:
5'-GCGATAAAGCTTCCACCATGAAGGTGATCATTGCAGC-3' (SEQ ID NO: 33)
HindIII*****

Oligodeoxynucleotide #10:
5'-GCGATAAAGCTTATTACTTCATGTTATCAC-3' (SEQ ID NO: 34)
HindIII Using approximately 3 μg of either cDNA clone plasmid as template, two separate PCR amplifications are carried out in the presence of the two oligodeoxynucleotide primers #9 and #10 as described above (Example 18, Part 2.), with however 18 instead of 38 cycles comprising cycling steps #1 through #3. The amplified coding sequences of inhibitor- 1 and inhibitor 2, which carry the optimized Kozak site but lack a complete polyadenylation signal (5'- . . . AATAAA . . . -3') found immediately 3' of the termination codon of the original cDNA clones, are then isolated and made suitable for ligation through digestion with the restriction endonuclease HindIII (Boehringer Mannheim) and subsequent extraction steps as described above (Example 18, Part 3.). 3 μg of plasmid DNA of the pMPSV/CMV-HE vector (Wirth, M., Schumacher, L., Hauser, H.: Construction of new expression vectors for mammalian cells using the immediate early enhancer of the human cytomegalovirus to increase expression from heterologous enhancer/promoters. In: Conradt, H. S. [Ed.], Protein Glycosylation: Cellular, Biotechnical and Analytical Aspects. Vol. 15, 49–52, VCH publishers, Weinheim, 1991; Kratzschmar, J., Haendler, B., Bringmann, P. Dinter, H. Hess, H., Donner, P., Schleuning, W.-D.: High-level secretion of the four salivary plasminogen activators from the vampire bat *Desmodus rotundus* by stably-transfected baby hamster kidney cells. Gene, (1992) 116; 281–284 are linearized through digestion with the restriction endonuclease HindIII and isolated as described. The recovered plasmid DNA is dephosphorylated using 1 unit of calf intestinal alkaline phosphatase (Boehringer Mannheim), subjected to the extraction procedure and then used for subcloning of the inhibitor-coding PCR fragments as described in Example 18, Part 3.

The DNA of the obtained pMPSV/CMV-inhibitor-1 or -2 constructs carrying HindIII inserts is digested with the restriction endonuclease EcoRI (Boehringer Mannheim) and in about half of the cases, an EcoRI restriction fragment of about 580 base pairs is seen, indicating those constructs where the inhibitor-coding insert is in the correct orientation with respect to the Myeloproliferative Sarcoma Virus promoter of the pMPSV/CMV vector. The complete inhibitor-coding inserts of such pMPSV/CMV-inhibitor-1 and -2 constructs are then sequenced using oligodeoxynucleotides #5 through #8 and two additional primers (oligodeoxynucleotides #11 and #12) derived from the insert-flanking region of the expression vector to check for mutations that might have been introduced during PCR amplification:

Oligodeoxynucleotide #11:
5'-ACCAGAAAGTTAACTGG-3' (SEQ ID NO: 35)

Oligodeoxynucleotide #12:
5'-CCTAGTTTGTGGTTGTCC-3' (SEQ ID. NO: 36)

Figure 11:
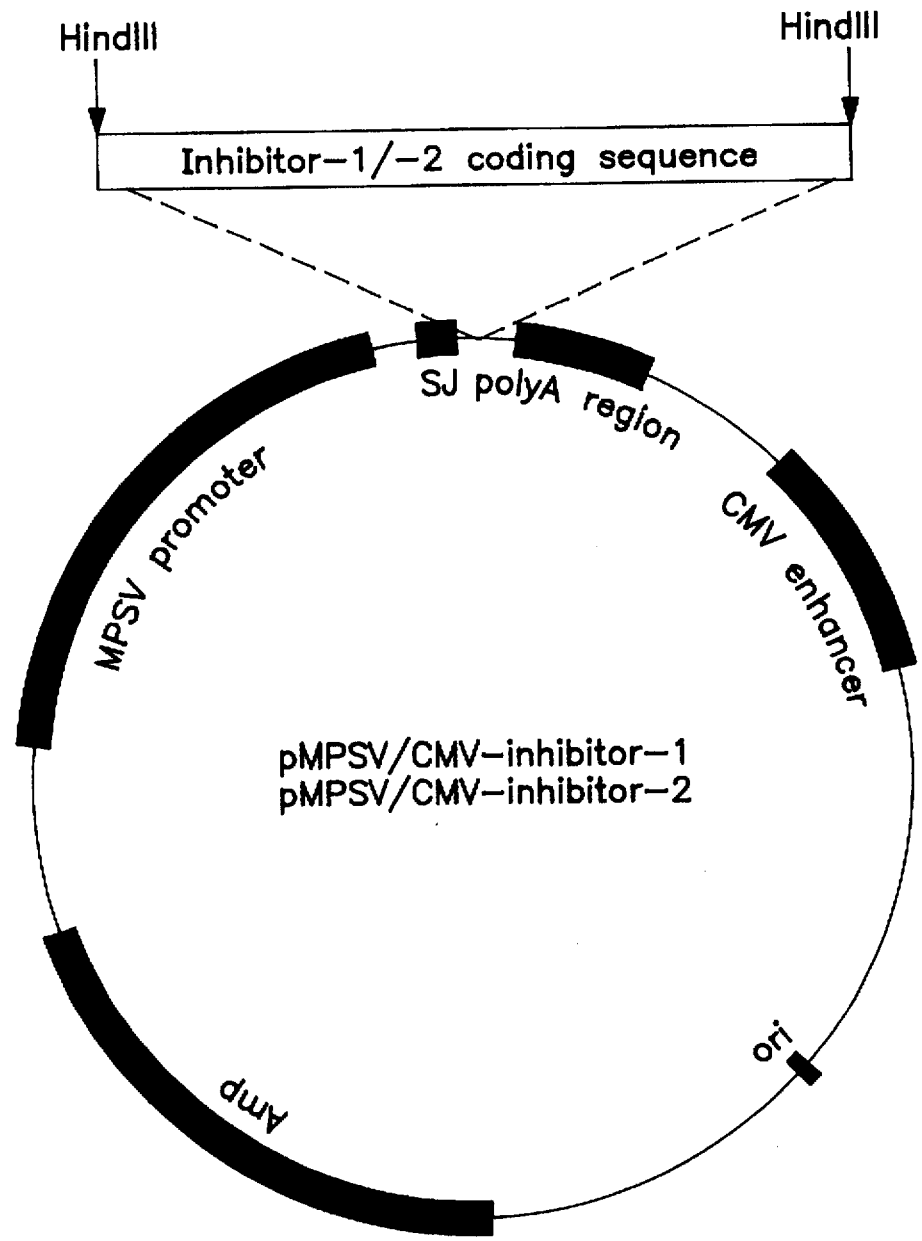
FIG. 11 shows the expression plasmid including the DNA coding for the inhibitor.

Two constructs for expression of inhibitor-1 and inhibitor-2 in mammalian cells coding for proteins identical in their amino acid sequence to those depicted in SEQ ID NOS:8 and 10 are thus obtained. A schematic map of the constructs is given in FIG. 11 ("Amp": ampicillin-resistance marker, "MPSV promoter": Myeloproliferative Sarcoma Virus promoter, "SJ": SV40 intron including its splice junctions, "polyA region": SV40 polyadenylation region, "CMV enhancer": cytomegalovirus enhancer, "ori": pBR322 origin of replication).

Part 2. Transfection and selection of BHK cells

Plasmid DNA of two resequenced pMPSV/CMV-inhibitor-1 and -2 constructs is isolated using "Qiagen-tip 100" columns (Qiagen Inc. Chatsworth, Calif., U.S.A.). Likewise, two plasmids that carry resistance marker genes, one for hygromycin B kinase (pSK/HMR272, constructed through subcloning of a BamHI-HindIII fragment containing the HSVtk promoter linked to the hygromycin B kinase gene into BluescriptSK, which fragment is taken from the pHMR272 vector described in: Bernhard, H. U., Kr ammer, G., Rowekamp, W. G.:Construction of a fusion gene that confers resistance against hygromycin B to mammalian cells in culture, Experimental Cell Research 158, 237–243, 1985) and the other for puromycin-N-acetyltransferase (pSV2pacDp; de la Luna, S., Soria, I., Pulido, D., Ortin, J., Jimenez, A.: Efficient transformation of mammalian cells with constructs containing a puromycin-resistance marker, Gene 62, 121–126, 1988), are prepared. Approximately 20 μg of the inhibitor-1 or -2 expression construct, 6 μg of the puromycin-resistance plasmid and 2 μg of the hygromycin-resistance plasmid are used for transfection of baby hamster kidney (BHK) cells as described (Kratzschmar, J., Haendler, B., Bringmann, P., Dinter, H., Hess, H., Donner, P., Schleuning, W.-D.: (1992) High-level secretion of the four salivary plasminogen activators from the vampire *Desmodus rotundus* by stably-transfected baby hamster kidney cells. Gene, 116, 281–284) using "Lipofectin™ Reagent" (Gibco-BRL Life Technologies). A double selection procedure is applied using DMEM/10% FCS (Gibco-BRL Life Technologies) containing 0.7 mg/ml of hygromycin B (Calbiochem Corporation, La Jolla, Calif., U.S.A.) and 5 μg/ml of puromycin (Sigma Chemical Company). The mixtures of double resistant BHK cells transfected with pMPSV/CMV-inhibitor-1 or -2 obtained after two weeks of selection are grown in serum-free OPTI-MEM (Gibco-BRL Life Technologies) as described (Kratzschmar, J., Haendler, B., Bringmann, P., Dinter, H., Hess, H., Donner, P., Schleuning, W.-D.: High-level secretion of the four salivary plasminogen activators from the vampire *Desmodus rotundus* by stably-transfected baby hamster kidney cells. Gene (1992) 116, 281–284). The conditioned media are collected after 24 hours, freed from cell debris through centrifugation at 2000 × g and stored frozen.

Part 3. Detection of recombinant inhibitor in BHK cell culture supernatants

Aliquots of the conditioned media are tested for inhibitor production in a Western blot (see Example 24). The anti-inhibitor antiserum reacts specifically with a 19 kDa protein present in the conditioned medium from pMPSV/CMV-inhibitor-1-transfected BHK cells from pMPSV/CMV-inhibitor-2-transfected BHK cells. No reaction is observed with control media from cells transfected with a pMPSV/CMV construct not containing the inhibitor insert or with fresh control medium. Extracts of the transfected cells give only a faint signal indicating that the recombinant proteins are secreted into the medium. Besides the immunological detection of the two recombinant inhibitor forms, the supernatants of the transfected BHK cells can also be tested in a functional assay. The inhibition of collagen-induced platelet aggregation can be measured in an aggregation assay as described in example 1.

Example 24

Antibody Production

About 100 μg of the inhibitor purified according to example 2 and 15 are added to 0.5 ml of complete Freund's adjuvant and the emulsion is injected s.c. into a rabbit. After 2 weeks a second injection is given consisting of about 80 μg purified inhibitor and 0.5 ml incomplete Freund's adjuvant. After the injection, several samples of serum are taken to check the production of specific antibodies. They are assayed in a Western blot. 20 ng of the purified inhibitor is applied on a 12.5% SDS-polyacrylamide gel and the electrophoresis, blotting and detection are done according to standard methods described by E. Harlowe, D. Lane, (1988) Antibodies: a laboratory manual, Cold Spring Harbor Laboratory (dilution of the test serum 1:500, goat anti rabbit peroxidase conjugated IgG as second antibody, detection with the ECL-kit from Amersham International, Amersham, UK). The blot shows that the antiserum specifically reacts with the purified inhibitor.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An isolated protein having the N-terminal amino acid sequence:

Glu—Glu—Cys—Glu—Leu—Met—Pro—Pro—Gly—Asp—
1                  5                                    10

Asn—Phe—Asp—Leu—Glu—Lys—Tyr—Phe—Ser—Ile
              14    15                                20

(amino acids 1-20 of SEQ ID NO:11), wherein the protein is encoded by a DNA molecule having a sequence which hybridizes with a DNA molecule of SEQ ID NO: 14, 15 or 16 under conditions wherein hybridization is conducted at 50° C. in the presence of 5 × SSC, 5 × Denhardt's solution, and 100 µg/ml salmon sperm DNA, and washing is conducted at 50° C. in 2 × SSC and 0.2% SDS, and wherein said protein inhibits collagen-induced aggregation of mammalian platelets.

2. An isolated protein which inhibits collagen-induced aggregation of mammalian platelets having the following amino acid sequence:
    a) the sequence in
        i) SEQ ID NO:11,
        ii) SEQ ID NO:12 or
        iii) SEQ ID NO;13,
or
    b) an amino acid sequence encoded by a DNA molecule having a sequence which hybridizes with a DNA molecule of SEQ ID NO: 14, 15 or 16 under conditions wherein hybridization is conducted at 50° C. in the presence of 5 × SSC, 5 × Denhardt's solution, and 100 µg/ml salmon sperm DNA, and washing is conducted at 50° C. in 2 × SSC and 0.2% SDS,
or
    c) a protein comprising a sequence of SEQ ID NO:11, 12 or 13 or a sequence as in b), and further comprising a posttranslational modification which does not substantially reduce the activity of the mature protein.

3. A protein of claim 1 which inhibits tumor cell-collagen interaction.

4. A protein of claim 2, which is recombinantly produced.

5. A protein of claim 4, which is unglycosylated.

6. A protein of claim 1, wherein said protein (a) is not fibrinogen-receptor antagonist;

(b) is not a thromboxane-antagonist;

(c) inhibits release-reaction of collagen-treated platelets;

(d) does not inhibit platelet aggregation induced by thrombin or ADP;

(e) does not react with collagen under in vivo conditions;

(f) has its platelet aggregation inhibition reversed by a large amount of collagen under in vitro conditions;

(g) has an inhibitory activity which is not influenced by protease-inhibitors;

(h) has an inhibitory activity which increases in the presence of $Mg^{2+}$ ions; and (i) is not cleavable by collagenase.

7. A protein of claim 6 which is a collagen receptor antagonist.

8. A protein of claim 1 which does not react with or bind to collagen in vivo.

9. A pharmaceutical composition comprising a protein of claim 1 and a pharmaceutically acceptable carrier.

10. A method of inhibiting collagen-induced human platelet aggregation comprising administering an effective amount of protein of claim 1.

11. A method of claim 10 for treating an atherosclerotic or thrombotic disease lesions or for preventing reocclusion after treatment of myocardial infarction.

12. A method of inhibiting tumor cell-collagen interaction comprising administering an effective amount of protein of claim 1.

13. A method of claim 12 for treating or preventing tumor cell metastasis.

14. A protein of claim 1 having an $IC_{50}$ for collagen-induced aggregation of at least 2.5 µg.

15. A collagen-induced platelet aggregation inhibitor protein having the amino acid sequence of SEQ ID NO:11, 12 or 13.

16. A protein of claim 15, produced by expression of a recombinant DNA sequence.

17. A protein of claim 16, wherein the DNA has the sequence of SEQ ID NO:14, 15 or 16.

18. A protein of claim 16, further comprising a precursor sequence, and said preprotein having the amino acid sequence of SEQ ID NO:8 or SEQ ID NO:10.

19. A preprotein of claim 18, produced by expression of a recombinant DNA sequence.

20. A preprotein of claim 19, wherein the DNA has the sequence SEQ ID NO: 17, 18 or 19.

21. A protein of claim 15, produced by cleavage of a preprotein.

22. A method of purifying a protein of claim 1, comprising separating the protein on a gel filtration column according to molecular size filtration, using no salt gradient; and chromatographing the protein on a high performance electrophoresis chromatography system.

23. A protein of claim 1, which is recombinantly produced.

24. A method of purifying a protein of claim 23, comprising separating the protein on a gel filtration column according to molecular size filtration, using no salt gradient; and chromatographing the protein on a high performance electrophoresis chromatography system.

25. A protein of claim 1, wherein said protein (a) is not fibrinogen-receptor antagonist;

(b) is not a thromboxane-antagonist;

(c) inhibits release-reaction of collagen-treated platelets;

(d) does not inhibit platelet aggregation induced by thrombin or ADP;

(e) does not react with collagen under in vivo conditions;

(f) has its platelet aggregation inhibition reversed by a large amount of collagen under in vitro conditions;

(g) has an inhibitory activity which is not influenced by protease-inhibitors;

(h) has an inhibitory activity which increases in the presence of $Mg^{2+}$ ions; or (i) is not cleavable by collagenase.

26. An isolated protein of claim 1, wherein the DNA molecule encodes a naturally occurring protein.

27. An isolated protein of claim 2, wherein the DNA molecule encodes a naturally occurring protein.

28. A pharmaceutical composition of claim 9, wherein the DNA molecule encodes a naturally occurring protein.

29. A method of claim 10, wherein the DNA molecule encodes a naturally occurring protein.

30. A method of claim 12, wherein the DNA molecule encodes a naturally occurring protein.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 528 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: TRIATOMA PALLIDIPENNIS ( x i ) SEQUENCE DESCRIPTION: SEQ ID NO:1:

```
ATGCCGCCGG GGGATAATTT CGATTTAGAA AAGTATTTCA GCATTCCTCA TGTGTATGTG        60
ACTCATTCAA GGAATGGACC AAAGGAACAA GTATGCCGAG AATATAAAAC TACAAAAAAT       120
TCAGATGGCA CCACCACAAC TACACTTGTG ACCTCAGATT ACAAAACTGG AGGAAAGCCG       180
TATCACTCTG AACTCAAGTG TACTAATACG CCGAAAAGTG GTGGTAAGGG TCAGTTTTCT       240
GTAGAATGCG AAGTACCAAA TGGAAACGGC GGTAAGAAGA AGATCCATGT AGAAACATCA       300
GTTATTGCTA CGGATTATAA AAACTATGCT TTACTTCAAA GTTGCACCAA GACTGAATCA       360
GGTATTGCAG ATGATGTTTT GCTATTGCAA ACAAAAAAAG AGGGCGTAGA CCCAGGAGTT       420
ACCTCTGTAC TTAAATCGGT CAATTGGTCC TTGGACGACT GGTTTTCCAG ATCAAAAGTT       480
ATTTGTGATA ACATGAAGTA ATAAATTTGT AAAAAAAAAA AAAAAAA                    528
```

( 2 ) INFORMATION FOR SEQ ID NO:2:

( i ) SEQUENCE CHARACTERISTICS:
        ( A ) LENGTH: 166 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 1

( D ) OTHER INFORMATION: /label= N- TERMINUS
/ note= "SEQUENCE BEGINS AT AA 6 OF MATURE PROTEIN"

( x i ) SEQUENCE DESCRIPTION: SEQ ID NO:2:

| Met | Pro | Pro | Gly | Asp | Asn | Phe | Asp | Leu | Glu | Lys | Tyr | Phe | Ser | Ile | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | Val | Tyr | Val | Thr | His | Ser | Arg | Asn | Gly | Pro | Lys | Glu | Gln | Val | Cys |
|     |     |     | 20  |     |     |     |     | 25  |     |     |     |     | 30  |     |     |
| Arg | Glu | Tyr | Lys | Thr | Thr | Lys | Asn | Ser | Asp | Gly | Thr | Thr | Thr | Thr | Thr |
|     |     | 35  |     |     |     |     | 40  |     |     |     |     | 45  |     |     |     |
| Leu | Val | Thr | Ser | Asp | Tyr | Lys | Thr | Gly | Gly | Lys | Pro | Tyr | His | Ser | Glu |
|     | 50  |     |     |     |     | 55  |     |     |     |     | 60  |     |     |     |     |
| Leu | Lys | Cys | Thr | Asn | Thr | Pro | Lys | Ser | Gly | Gly | Lys | Gly | Gln | Phe | Ser |
| 65  |     |     |     |     | 70  |     |     |     |     | 75  |     |     |     |     | 80  |
| Val | Glu | Cys | Glu | Val | Pro | Asn | Gly | Asn | Gly | Gly | Lys | Lys | Lys | Ile | His |
|     |     |     |     | 85  |     |     |     |     | 90  |     |     |     |     | 95  |     |
| Val | Glu | Thr | Ser | Val | Ile | Ala | Thr | Asp | Tyr | Lys | Asn | Tyr | Ala | Leu | Leu |
|     |     |     | 100 |     |     |     |     | 105 |     |     |     |     | 110 |     |     |
| Gln | Ser | Cys | Thr | Lys | Thr | Glu | Ser | Gly | Ile | Ala | Asp | Asp | Val | Leu | Leu |
|     |     | 115 |     |     |     |     | 120 |     |     |     |     | 125 |     |     |     |
| Leu | Gln | Thr | Lys | Lys | Glu | Gly | Val | Asp | Pro | Gly | Val | Thr | Ser | Val | Leu |
|     | 130 |     |     |     |     | 135 |     |     |     |     | 140 |     |     |     |     |
| Lys | Ser | Val | Asn | Trp | Ser | Leu | Asp | Asp | Trp | Phe | Ser | Arg | Ser | Lys | Val |
| 145 |     |     |     |     | 150 |     |     |     |     | 155 |     |     |     |     | 160 |
| Asn | Cys | Asp | Asn | Met | Lys |     |     |     |     |     |     |     |     |     |     |
|     |     |     |     | 165 |     |     |     |     |     |     |     |     |     |     |     |

( 2 ) INFORMATION FOR SEQ ID NO:3:

( i ) SEQUENCE CHARACTERISTICS:
        ( A ) LENGTH: 524 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| ATGCCGCCGG | GGGATAATTT | CGATTTAGAA | AAGTATTTCA | GCATTCCTCA | TGTGTATGTG | 60  |
|------------|------------|------------|------------|------------|------------|-----|
| ACTCATTCAA | GGAATGGACC | AAAGGAACAA | GTATGCCGAG | AATATAAAAC | TACAAAAAAT | 120 |
| TCAGATGGCA | CCACAACTAC | ACTTGTGACC | TCAGATTACA | AAACTGGAGG | AAAGCCGTAT | 180 |
| CACTCTGAAC | TCAAGTGTAC | TAATACGCCG | AAAAGTGGTG | TTAAGGGTCA | GTTTCTGTA  | 240 |
| GAATGCGAAG | TACCAAATGG | AAACGGCGGT | AAGAAGAAGA | TCCATGTAGA | AACATCAGTT | 300 |
| ATTGCTACGG | ATTATAAAAA | CTATGCTTTA | CTTCAAAGTT | GCACCAAGAC | TGAATCAGGT | 360 |
| ATTGCAGATG | ATGTTTTGCT | ATTGCAAACA | AAAAAGAGG  | GCGTAGACCC | AGGAGTTACC | 420 |
| TCTGTACTTA | AATCGGTCAA | TTGGTCCTTG | GACGACTGGT | TTTCCAGATC | AAAAGTTATT | 480 |
| TGTGATAACA | TGAAGTAATA | AATTTGTAAA | AAAAAAAAAA | AAAA       |            | 524 |

( 2 ) INFORMATION FOR SEQ ID NO:4:

( i ) SEQUENCE CHARACTERISTICS:
        ( A ) LENGTH: 165 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Region
    ( B ) LOCATION: 1
    ( D ) OTHER INFORMATION: /label= N- TERMINUS
        / note= "SEQUENCE BEGINS WITH AA 6 OF PROTEIN"

( x i ) SEQUENCE DESCRIPTION: SEQ ID NO:4:

```
Met Pro Pro Gly Asp Asn Phe Asp Leu Glu Lys Tyr Phe Ser Ile Pro
 1            5                    10                   15

His Val Tyr Val Thr His Ser Arg Asn Gly Pro Lys Glu Gln Val Cys
            20                  25              30

Arg Glu Tyr Lys Thr Thr Lys Asn Ser Asp Gly Thr Thr Thr Thr Leu
         35              40              45

Val Thr Ser Asp Tyr Lys Thr Gly Gly Lys Pro Tyr His Ser Glu Leu
     50              55              60

Lys Cys Thr Asn Thr Pro Lys Ser Gly Val Lys Gly Gln Phe Ser Val
 65              70              75                         80

Glu Cys Glu Val Pro Asn Gly Asn Gly Gly Lys Lys Lys Ile His Val
                 85              90                       95

Glu Thr Ser Val Ile Ala Thr Asp Tyr Lys Asn Tyr Ala Leu Leu Gln
             100             105             110

Ser Cys Thr Lys Thr Glu Ser Gly Ile Ala Asp Asp Val Leu Leu Leu
         115             120             125

Gln Thr Lys Lys Glu Gly Val Asp Pro Gly Val Thr Ser Val Leu Lys
     130             135             140

Ser Val Asn Trp Ser Leu Asp Asp Trp Phe Ser Arg Ser Lys Val Asn
145             150             155                     160

Cys Asp Asn Met Lys
                165
```

( 2 ) INFORMATION FOR SEQ ID NO:5:

( i ) SEQUENCE CHARACTERISTICS:
        ( A ) LENGTH: 530 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
ATGCCGCCGG GGGATAATTT CGATTTAGAA AAGTATTTCA GCATTCCTCA TGTGTATGTG      60
ACTCATTCAA GGAATGGACC AAAGGAACAA GTATGCCGAG AATATAAAAC TACAAAAAAT     120
TCAGATGGCA CCACCACAAC TACACTTGTG ACCTCAGATT ACAAAACTGG AGGAAAGCCG     180
TATCACTCTG AACTCAAGTG TACTAATACG CAGAAAAGTG GTGGTAAGGG TCAGTTTTCT     240
GTAGAATGCG AAGTACCAAA TGGAAACGGC GGTAAGAAGA AGATCCATGT AGAAACATCA     300
GTTATTGCTA CGGATTATAA AAACTATGCT TTACTTCAAA GTTGCACCAA GACTGAATCA     360
GGTATTGCAG ATGATGTTTT GCTATTGCAA ACAAAAAAAG AGGGCGTAGA CCCAGGAGTT     420
ACCTCTGTAC TTAAATCGGT CAATTGGTCC TTGGACGACT GGTTTTCCAG ATCAAAAGTT     480
ATTTGTGATA ACATGAAGTA ATAAATTTGT AAAAAAAAAA AAAAAAAAA                 530
```

( 2 ) INFORMATION FOR SEQ ID NO:6:

( i ) SEQUENCE CHARACTERISTICS:
        ( A ) LENGTH: 166 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Region
    ( B ) LOCATION: 1
    ( D ) OTHER INFORMATION: /label= N- TERMINUS
       / note= "SEQUENCE BEGINS AT AA 6 OF PROTEIN"

( x i ) SEQUENCE DESCRIPTION: SEQ ID NO:6:

```
Met Pro Pro Gly Asp Asn Phe Asp Leu Glu Lys Tyr Phe Ser Ile Pro
 1            5                    10                   15
His Val Tyr Val Thr His Ser Arg Asn Gly Pro Lys Glu Gln Val Cys
             20                25                   30
Arg Glu Tyr Lys Thr Thr Lys Asn Ser Asp Gly Thr Thr Thr Thr Thr
         35                   40                45
Leu Val Thr Ser Asp Tyr Lys Thr Gly Gly Lys Pro Tyr His Ser Glu
     50                   55              60
Leu Lys Cys Thr Asn Thr Gln Lys Ser Gly Gly Lys Gly Gln Phe Ser
 65              70                   75                   80
Val Glu Cys Glu Val Pro Asn Gly Asn Gly Gly Lys Lys Lys Ile His
                 85                   90                   95
Val Glu Thr Ser Val Ile Ala Thr Asp Tyr Lys Asn Tyr Ala Leu Leu
             100                  105                  110
Gln Ser Cys Thr Lys Thr Glu Ser Gly Ile Ala Asp Asp Val Leu Leu
             115                  120                  125
Leu Gln Thr Lys Lys Glu Gly Val Asp Pro Gly Val Thr Ser Val Leu
         130                  135                  140
Lys Ser Val Asn Trp Ser Leu Asp Asp Trp Phe Ser Arg Ser Lys Val
145                  150                  155                  160
Asn Cys Asp Asn Met Lys
                 165
```

( 2 ) INFORMATION FOR SEQ ID NO:7:

( i ) SEQUENCE CHARACTERISTICS:
        ( A ) LENGTH: 588 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
ATGAAGGTGA TCATTGCAGC AACATTACTT GGAATTCTGA TGCATGCATT TGCTGAAGAA    60
TGCGAACTCA TGCCACCAGG GGATAACTTT GATTTAGAAA AGTATTTCAG CATTCCTCAT   120
GTGTATGTGA CTCATTCAAG GAATGGACCA AAGGAACAAG TATGCCGAGA ATATAAAACT   180
ACAAAAAATT CAGATGGCAC CACCACAACT ACACTTGTGA CCTCAGATTA CAAAACTGGA   240
GGAAAGCCGT ATCACTCTGA ACTCAAGTGT ACTAATACGC CGAAAAGTGG TGGTAAGGGT   300
CAGTTTTCTG TAGAATGCGA AGTACCAAAT GGAAACGGCG GTAAGAAGAA GATCCATGTA   360
GAAACATCAG TTATTGCTAC GGATTATAAA ACTATGCTT TACTTCAAAG TTGCACCAAG    420
ACTGAATCAG GTATTGCAGA TGATGTTTTG CTATTGCAAA CAAAAAAAGA GGGCGTAGAC   480
CCAGGAGTTA CCTCTGTACT TAAATCGGTC AATTGGTCCT TGGACGACTG GTTTCCAGA    540
TCAAAAGTTA TTTGTGATAA CATGAAGTAA TAAATTTGTA AAAAAAA                 588
```

( 2 ) INFORMATION FOR SEQ ID NO:8:

( i ) SEQUENCE CHARACTERISTICS:
   ( A ) LENGTH: 189 amino acids
   ( B ) TYPE: amino acid
   ( C ) STRANDEDNESS: single
   ( D ) TOPOLOGY: linear ( i i ) MOLECULE TYPE: protein ( i x ) FEATURE:
   ( A ) NAME/KEY: Protein
   ( B ) LOCATION: 19..189

( x i ) SEQUENCE DESCRIPTION: SEQ ID NO:8:

```
Met  Lys  Val  Ile  Ile  Ala  Ala  Thr  Leu  Leu  Gly  Ile  Leu  Met  His  Ala
              -15                      -10                       -5
Phe  Ala  Glu  Glu  Cys  Glu  Leu  Met  Pro  Pro  Gly  Asp  Asn  Phe  Asp  Leu
          1                    5                       10
Glu  Lys  Tyr  Phe  Ser  Ile  Pro  His  Val  Tyr  Val  Thr  His  Ser  Arg  Asn
15                       20                      25                       30
Gly  Pro  Lys  Glu  Gln  Val  Cys  Arg  Glu  Tyr  Lys  Thr  Thr  Lys  Asn  Ser
                35                      40                       45
Asp  Gly  Thr  Thr  Thr  Thr  Thr  Leu  Val  Thr  Ser  Asp  Tyr  Lys  Thr  Gly
               50                       55                       60
Gly  Lys  Pro  Tyr  His  Ser  Glu  Leu  Lys  Cys  Thr  Asn  Thr  Pro  Lys  Ser
          65                       70                       75
Gly  Gly  Lys  Gly  Gln  Phe  Ser  Val  Glu  Cys  Glu  Val  Pro  Asn  Gly  Asn
80                            85                       90
Gly  Gly  Lys  Lys  Lys  Ile  His  Val  Glu  Thr  Ser  Val  Ile  Ala  Thr  Asp
95                       100                      105                      110
Tyr  Lys  Asn  Tyr  Ala  Leu  Leu  Gln  Ser  Cys  Thr  Lys  Thr  Glu  Ser  Gly
               115                      120                      125
Ile  Ala  Asp  Asp  Val  Leu  Leu  Leu  Gln  Thr  Lys  Lys  Glu  Gly  Val  Asp
               130                      135                      140
Pro  Gly  Val  Thr  Ser  Val  Leu  Lys  Ser  Val  Asn  Trp  Ser  Leu  Asp  Asp
          145                      150                      155
Trp  Phe  Ser  Arg  Ser  Lys  Val  Asn  Cys  Asp  Asn  Met  Lys
160                      165                      170
```

( 2 ) INFORMATION FOR SEQ ID NO:9:

( i ) SEQUENCE CHARACTERISTICS:
       ( A ) LENGTH: 586 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:9:

```
ATGAAGGTGA TCATTGCAGC AACATTACTT GGAATTCTGA TGCATGCATT TGCTGAAGAA    60
TGCGAACTCA TGCCACCAGG GGATAACTTT GATTTAGAAA AGTATTTCAG CATTCCTCAT   120
GTGTATGTGA CTCATTCAAG GAATGGACCA AAGGAACAAG TATGCCGAGA ATATAAAACT   180
ACAAAAAATT CAGATGGCAC CACAACTACA CTTGTGACCT CAGATTACAA AACTGGAGGA   240
AAGCCGTATC ACTCTGAACT CAAGTGTACT AATACGCCGA AAGTGGTGT TAAGGGTCAG    300
TTTTCTGTAG AATGCGAAGT ACCAAATGGA AACGGCGGTA AGAAGAAGAT CCATGTAGAA   360
ACATCAGTTA TTGCTACGGA TTATAAAAAC TATGCTTTAC TTCAAAGTTG CACCAAGACT   420
GAATCAGGTA TTGCAGATGA TGTTTTGCTA TTGCAAACAA AAAAAGAGGG CGTAGACCCA   480
GGAGTTACCT CTGTACTTAA ATCGGTCAAT TGGTCCTTGG ACGACTGGTT TTCCAGATCA   540
```

AAAGTTATTT GTGATAACAT GAAGTAATAA ATTTGTAAAA AAAAAA        586

( 2 ) INFORMATION FOR SEQ ID NO:10:

( i ) SEQUENCE CHARACTERISTICS:
      ( A ) LENGTH: 188 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 19..188

( x i ) SEQUENCE DESCRIPTION: SEQ ID NO:10:

| Met | Lys | Val | Ile  | Ile | Ala | Ala | Thr | Leu  | Leu | Gly | Ile | Leu | Met | His | Ala |
|     |     |     | -15  |     |     |     |     | -10  |     |     |     |     | -5  |     |     |
| Phe | Ala | Glu | Glu  | Cys | Glu | Leu | Met | Pro  | Pro | Gly | Asp | Asn | Phe | Asp | Leu |
|     |     | 1   |      |     |     | 5   |     |      |     |     | 10  |     |     |     |     |
| Glu | Lys | Tyr | Phe  | Ser | Ile | Pro | His | Val  | Tyr | Val | Thr | His | Ser | Arg | Asn |
| 15  |     |     |      |     | 20  |     |     |      |     | 25  |     |     |     |     | 30  |
| Gly | Pro | Lys | Glu  | Gln | Val | Cys | Arg | Glu  | Tyr | Lys | Thr | Thr | Lys | Asn | Ser |
|     |     |     |      | 35  |     |     |     |      | 40  |     |     |     |     | 45  |     |
| Asp | Gly | Thr | Thr  | Thr | Thr | Leu | Val | Thr  | Ser | Asp | Tyr | Lys | Thr | Gly | Gly |
|     |     |     | 50   |     |     |     |     | 55   |     |     |     |     | 60  |     |     |
| Lys | Pro | Tyr | His  | Ser | Glu | Leu | Lys | Cys  | Thr | Asn | Thr | Pro | Lys | Ser | Gly |
|     |     |     | 65   |     |     |     | 70  |      |     |     |     | 75  |     |     |     |
| Val | Lys | Gly | Gln  | Phe | Ser | Val | Glu | Cys  | Glu | Val | Pro | Asn | Gly | Asn | Gly |
|     |     | 80  |      |     |     |     | 85  |      |     |     | 90  |     |     |     |     |
| Gly | Lys | Lys | Lys  | Ile | His | Val | Glu | Thr  | Ser | Val | Ile | Ala | Thr | Asp | Tyr |
| 95  |     |     |      |     | 100 |     |     |      |     | 105 |     |     |     |     | 110 |
| Lys | Asn | Tyr | Ala  | Leu | Leu | Gln | Ser | Cys  | Thr | Lys | Thr | Glu | Ser | Gly | Ile |
|     |     |     |      | 115 |     |     |     |      | 120 |     |     |     |     | 125 |     |
| Ala | Asp | Asp | Val  | Leu | Leu | Leu | Gln | Thr  | Lys | Lys | Glu | Gly | Val | Asp | Pro |
|     |     |     | 130  |     |     |     |     | 135  |     |     |     |     | 140 |     |     |
| Gly | Val | Thr | Ser  | Val | Leu | Lys | Ser | Val  | Asn | Trp | Ser | Leu | Asp | Asp | Trp |
|     |     |     | 145  |     |     |     |     | 150  |     |     |     |     | 155 |     |     |
| Phe | Ser | Arg | Ser  | Lys | Val | Asn | Cys | Asp  | Asn | Met | Lys |     |     |     |     |
|     |     |     | 160  |     |     |     | 165 |      |     |     | 170 |     |     |     |     |

( 2 ) INFORMATION FOR SEQ ID NO:11:

( i ) SEQUENCE CHARACTERISTICS:
      ( A ) LENGTH: 171 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:11:

| Glu | Glu | Cys | Glu | Leu | Met | Pro | Pro | Gly | Asn | Phe | Asp | Leu | Glu | Lys |
| 1   |     |     |     | 5   |     |     |     |     | 10  |     |     |     |     | 15  |
| Tyr | Phe | Ser | Ile | Pro | His | Val | Tyr | Val | Thr | His | Ser | Arg | Asn | Gly | Pro |
|     |     |     | 20  |     |     |     |     | 25  |     |     |     |     | 30  |     |     |
| Lys | Glu | Gln | Val | Cys | Arg | Glu | Tyr | Lys | Thr | Thr | Lys | Asn | Ser | Asp | Gly |
|     |     | 35  |     |     |     |     | 40  |     |     |     |     | 45  |     |     |     |
| Thr | Thr | Thr | Thr | Thr | Leu | Val | Thr | Ser | Asp | Tyr | Lys | Thr | Gly | Gly | Lys |
|     |     |     | 50  |     |     |     |     | 55  |     |     |     |     | 60  |     |     |

```
Pro  Tyr  His  Ser  Glu  Leu  Lys  Cys  Thr  Asn  Thr  Pro  Lys  Ser  Gly  Gly
65             70                  75                  80

Lys  Gly  Gln  Phe  Ser  Val  Glu  Cys  Glu  Val  Pro  Asn  Gly  Asn  Gly  Gly
                    85                  90                       95

Lys  Lys  Lys  Ile  His  Val  Glu  Thr  Ser  Val  Ile  Ala  Thr  Asp  Tyr  Lys
               100                 105                      110

Asn  Tyr  Ala  Leu  Leu  Gln  Ser  Cys  Thr  Lys  Thr  Glu  Ser  Gly  Ile  Ala
          115                 120                      125

Asp  Asp  Val  Leu  Leu  Leu  Gln  Thr  Lys  Lys  Glu  Gly  Val  Asp  Pro  Gly
     130                      135                 140

Val  Thr  Ser  Val  Leu  Lys  Ser  Val  Asn  Trp  Ser  Leu  Asp  Asp  Trp  Phe
145                      150                 155                      160

Ser  Arg  Ser  Lys  Val  Asn  Cys  Asp  Asn  Met  Lys
                    165                 170
```

(2) INFORMATION FOR SEQ ID NO:12:

(i) SEQUENCE CHARACTERISTICS:
    (A) LENGTH: 170 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:12:

```
Glu  Glu  Cys  Glu  Leu  Met  Pro  Pro  Gly  Asp  Asn  Phe  Asp  Leu  Glu  Lys
1              5                   10                      15

Tyr  Phe  Ser  Ile  Pro  His  Val  Tyr  Val  Thr  His  Ser  Arg  Asn  Gly  Pro
               20                  25                      30

Lys  Glu  Gln  Val  Cys  Arg  Glu  Tyr  Lys  Thr  Thr  Lys  Asn  Ser  Asp  Gly
          35                  40                      45

Thr  Thr  Thr  Thr  Leu  Val  Thr  Ser  Asp  Tyr  Lys  Thr  Gly  Gly  Lys  Pro
     50                      55                 60

Tyr  His  Ser  Glu  Leu  Lys  Cys  Thr  Asn  Thr  Pro  Lys  Ser  Gly  Val  Lys
65                       70                 75                       80

Gly  Gln  Phe  Ser  Val  Glu  Cys  Glu  Val  Pro  Asn  Gly  Asn  Gly  Gly  Lys
                    85                  90                      95

Lys  Lys  Ile  His  Val  Glu  Thr  Ser  Val  Ile  Ala  Thr  Asp  Tyr  Lys  Asn
               100                 105                      110

Tyr  Ala  Leu  Leu  Gln  Ser  Cys  Thr  Lys  Thr  Glu  Ser  Gly  Ile  Ala  Asp
          115                 120                      125

Asp  Val  Leu  Leu  Leu  Gln  Thr  Lys  Lys  Glu  Gly  Val  Asp  Pro  Gly  Val
     130                      135                 140

Thr  Ser  Val  Leu  Lys  Ser  Val  Asn  Trp  Ser  Leu  Asp  Asp  Trp  Phe  Ser
145                      150                 155                      160

Arg  Ser  Lys  Val  Asn  Cys  Asp  Asn  Met  Lys
                    165                 170
```

(2) INFORMATION FOR SEQ ID NO:13:

(i) SEQUENCE CHARACTERISTICS:
    (A) LENGTH: 171 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:13:

|       |       |       |       |       |       |       |       |       |       |       |       |       |       |       |
|-------|-------|-------|-------|-------|-------|-------|-------|-------|-------|-------|-------|-------|-------|-------|
| Glu   | Glu   | Cys   | Glu   | Leu   | Met   | Pro   | Pro   | Gly   | Asp   | Asn   | Phe   | Asp   | Leu   | Glu   | Lys |
| 1     |       |       |       | 5     |       |       |       |       | 10    |       |       |       |       | 15    |
| Tyr   | Phe   | Ser   | Ile   | Pro   | His   | Val   | Tyr   | Val   | Thr   | His   | Ser   | Arg   | Asn   | Gly   | Pro |
|       |       |       | 20    |       |       |       |       | 25    |       |       |       |       | 30    |       |
| Lys   | Glu   | Gln   | Val   | Cys   | Arg   | Glu   | Tyr   | Lys   | Thr   | Thr   | Lys   | Asn   | Ser   | Asp   | Gly |
|       |       | 35    |       |       |       |       | 40    |       |       |       |       | 45    |       |       |
| Thr   | Thr   | Thr   | Thr   | Thr   | Leu   | Val   | Thr   | Ser   | Asp   | Tyr   | Lys   | Thr   | Gly   | Gly   | Lys |
|       | 50    |       |       |       |       | 55    |       |       |       |       | 60    |       |       |       |
| Pro   | Tyr   | His   | Ser   | Glu   | Leu   | Lys   | Cys   | Thr   | Asn   | Thr   | Gln   | Lys   | Ser   | Gly   | Gly |
| 65    |       |       |       |       | 70    |       |       |       |       | 75    |       |       |       |       | 80  |
| Lys   | Gly   | Gln   | Phe   | Ser   | Val   | Glu   | Cys   | Glu   | Val   | Pro   | Asn   | Gly   | Asn   | Gly   | Gly |
|       |       |       |       | 85    |       |       |       |       | 90    |       |       |       |       | 95    |     |
| Lys   | Lys   | Lys   | Ile   | His   | Val   | Glu   | Thr   | Ser   | Val   | Ile   | Ala   | Thr   | Asp   | Tyr   | Lys |
|       |       |       | 100   |       |       |       |       | 105   |       |       |       |       | 110   |       |     |
| Asn   | Tyr   | Ala   | Leu   | Leu   | Gln   | Ser   | Cys   | Thr   | Lys   | Thr   | Glu   | Ser   | Gly   | Ile   | Ala |
|       |       | 115   |       |       |       |       | 120   |       |       |       |       | 125   |       |       |     |
| Asp   | Asp   | Val   | Leu   | Leu   | Leu   | Gln   | Thr   | Lys   | Lys   | Glu   | Gly   | Val   | Asp   | Pro   | Gly |
|       | 130   |       |       |       |       | 135   |       |       |       |       | 140   |       |       |       |     |
| Val   | Thr   | Ser   | Val   | Leu   | Lys   | Ser   | Val   | Asn   | Trp   | Ser   | Leu   | Asp   | Asp   | Trp   | Phe |
| 145   |       |       |       |       | 150   |       |       |       |       | 155   |       |       |       |       | 160 |
| Ser   | Arg   | Ser   | Lys   | Val   | Asn   | Cys   | Asp   | Asn   | Met   | Lys   |       |       |       |       |     |
|       |       |       |       | 165   |       |       |       |       | 170   |       |       |       |       |       |     |

( 2 ) INFORMATION FOR SEQ ID NO:14:

( i ) SEQUENCE CHARACTERISTICS:
        ( A ) LENGTH: 516 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
GAAGAATGCG AACTCATGCC ACCAGGGGAT AACTTTGATT TAGAAAAGTA TTTCAGCATT        60
CCTCATGTGT ATGTGACTCA TTCAAGGAAT GGACCAAAGG AACAAGTATG CCGAGAATAT       120
AAAACTACAA AAAATTCAGA TGGCACCACC ACAACTACAC TTGTGACCTC AGATTACAAA       180
ACTGGAGGAA AGCCGTATCA CTCTGAACTC AAGTGTACTA ATACGCCGAA AAGTGGTGGT       240
AAGGGTCAGT TTTCTGTAGA ATGCGAAGTA CCAAATGGAA ACGGCGGTAA GAAGAAGATC       300
CATGTAGAAA CATCAGTTAT TGCTACGGAT TATAAAAACT ATGCTTTACT TCAAAGTTGC       360
ACCAAGACTG AATCAGGTAT TGCAGATGAT GTTTTGCTAT TGCAAACAAA AAAAGAGGGC       420
GTAGACCCAG GAGTTACCTC TGTACTTAAA TCGGTCAATT GGTCCTTGGA CGACTGGTTT       480
TCCAGATCAA AAGTTATTTG TGATAACATG AAGTAA                                 516
```

( 2 ) INFORMATION FOR SEQ ID NO:15:

( i ) SEQUENCE CHARACTERISTICS:
        ( A ) LENGTH: 513 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

```
GAAGAATGCG AACTCATGCC ACCAGGGGAT AACTTTGATT TAGAAAAGTA TTTCAGCATT        60
```

```
CCTCATGTGT ATGTGACTCA TTCAAGGAAT GGACCAAAGG AACAAGTATG CCGAGAATAT    120

AAAACTACAA AAAATTCAGA TGGCACCACA ACTACACTTG TGACCTCAGA TTACAAAACT    180

GGAGGAAAGC CGTATCACTC TGAACTCAAG TGTACTAATA CGCCGAAAAG TGGTGTTAAG    240

GGTCAGTTTT CTGTAGAATG CGAAGTACCA AATGGAAACG GCGGTAAGAA GAAGATCCAT    300

GTAGAAACAT CAGTTATTGC TACGGATTAT AAAAACTATG CTTTACTTCA AGTTGCACC    360

AAGACTGAAT CAGGTATTGC AGATGATGTT TTGCTATTGC AAACAAAAAA AGAGGGCGTA    420

GACCCAGGAG TTACCTCTGT ACTTAAATCG GTCAATTGGT CCTTGGACGA CTGGTTTTCC    480

AGATCAAAAG TTATTTGTGA TAACATGAAG TAA                                 513
```

( 2 ) INFORMATION FOR SEQ ID NO:16:

( i ) SEQUENCE CHARACTERISTICS:
        ( A ) LENGTH: 516 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
GAAGAATGCG AACTCATGCC ACCAGGGGAT AACTTTGATT TAGAAAAGTA TTTCAGCATT    60

CCTCATGTGT ATGTGACTCA TTCAAGGAAT GGACCAAAGG AACAAGTATG CCGAGAATAT    120

AAAACTACAA AAAATTCAGA TGGCACCACC ACAACTACAC TTGTGACCTC AGATTACAAA    180

ACTGGAGGAA AGCCGTATCA CTCTGAACTC AAGTGTACTA ATACGCAGAA AAGTGGTGGT    240

AAGGGTCAGT TTTCTGTAGA ATGCGAAGTA CCAAATGGAA ACGGCGGTAA GAAGAAGATC    300

CATGTAGAAA CATCAGTTAT TGCTACGGAT TATAAAAACT ATGCTTTACT TCAAAGTTGC    360

ACCAAGACTG AATCAGGTAT TGCAGATGAT GTTTTGCTAT TGCAAACAAA AAAAGAGGGC    420

GTAGACCCAG GAGTTACCTC TGTACTTAAA TCGGTCAATT GGTCCTTGGA CGACTGGTTT    480

TCCAGATCAA AAGTTATTTG TGATAACATG AAGTAA                              516
```

( 2 ) INFORMATION FOR SEQ ID NO:17:

( i ) SEQUENCE CHARACTERISTICS:
        ( A ) LENGTH: 570 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
ATGAAGGTGA TCATTGCAGC AACATTACTT GGAATTCTGA TGCATGCATT TGCTGAAGAA    60

TGCGAACTCA TGCCACCAGG GGATAACTTT GATTTAGAAA AGTATTTCAG CATTCCTCAT    120

GTGTATGTGA CTCATTCAAG GAATGGACCA AAGGAACAAG TATGCCGAGA ATATAAAACT    180

ACAAAAAATT CAGATGGCAC CACCACAACT ACACTTGTGA CCTCAGATTA CAAAACTGGA    240

GGAAAGCCGT ATCACTCTGA ACTCAAGTGT ACTAATACGC CGAAAAGTGG TGGTAAGGGT    300

CAGTTTTCTG TAGAATGCGA AGTACCAAAT GGAAACGGCG GTAAGAAGAA GATCCATGTA    360

GAAACATCAG TTATTGCTAC GGATTATAAA AACTATGCTT TACTTCAAAG TTGCACCAAG    420

ACTGAATCAG GTATTGCAGA TGATGTTTTG CTATTGCAAA CAAAAAAAGA GGGCGTAGAC    480

CCAGGAGTTA CCTCTGTACT TAAATCGGTC AATTGGTCCT TGGACGACTG GTTTTCCAGA    540

TCAAAAGTTA TTTGTGATAA CATGAAGTAA                                     570
```

( 2 ) INFORMATION FOR SEQ ID NO:18:

( i ) SEQUENCE CHARACTERISTICS:
        ( A ) LENGTH: 567 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

```
ATGAAGGTGA TCATTGCAGC AACATTACTT GGAATTCTGA TGCATGCATT TGCTGAAGAA      60
TGCGAACTCA TGCCACCAGG GGATAACTTT GATTTAGAAA AGTATTTCAG CATTCCTCAT     120
GTGTATGTGA CTCATTCAAG GAATGGACCA AAGGAACAAG TATGCCGAGA ATATAAAACT     180
ACAAAAAATT CAGATGGCAC CACAACTACA CTTGTGACCT CAGATTACAA AACTGGAGGA     240
AAGCCGTATC ACTCTGAACT CAAGTGTACT AATACGCCGA AAAGTGGTGT TAAGGGTCAG     300
TTTTCTGTAG AATGCGAAGT ACCAAATGGA AACGGCGGTA GAAGAAGAT CCATGTAGAA      360
ACATCAGTTA TTGCTACGGA TTATAAAAAC TATGCTTTAC TTCAAAGTTG CACCAAGACT     420
GAATCAGGTA TTGCAGATGA TGTTTTGCTA TTGCAAACAA AAAAGAGGG CGTAGACCCA      480
GGAGTTACCT CTGTACTTAA ATCGGTCAAT TGGTCCTTGG ACGACTGGTT TTCCAGATCA     540
AAAGTTATTT GTGATAACAT GAAGTAA                                        567
```

( 2 ) INFORMATION FOR SEQ ID NO:19:

( i ) SEQUENCE CHARACTERISTICS:
        ( A ) LENGTH: 570 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

```
ATGAAGGTGA TCATTGCAGC AACATTACTT GGAATTCTGA TGCATGCATT TGCTGAAGAA      60
TGCGAACTCA TGCCACCAGG GGATAACTTT GATTTAGAAA AGTATTTCAG CATTCCTCAT     120
GTGTATGTGA CTCATTCAAG GAATGGACCA AAGGAACAAG TATGCCGAGA ATATAAAACT     180
ACAAAAAATT CAGATGGCAC CACCACAACT ACACTTGTGA CCTCAGATTA CAAAACTGGA     240
GGAAAGCCGT ATCACTCTGA ACTCAAGTGT ACTAATACGC AGAAAAGTGG TGGTAAGGGT     300
CAGTTTTCTG TAGAATGCGA AGTACCAAAT GGAAACGGCG GTAAGAAGAA GATCCATGTA     360
GAAACATCAG TTATTGCTAC GGATTATAAA ACTATGCTT TACTTCAAAG TTGCACCAAG      420
ACTGAATCAG GTATTGCAGA TGATGTTTTG CTATTGCAAA CAAAAAAAGA GGGCGTAGAC     480
CCAGGAGTTA CCTCTGTACT TAAATCGGTC AATTGGTCCT TGGACGACTG GTTTTCCAGA     540
TCAAAAGTTA TTTGTGATAA CATGAAGTAA                                      570
```

( 2 ) INFORMATION FOR SEQ ID NO:20:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1

( D ) OTHER INFORMATION: /label= N- TERMINUS
/ note= "SEQUENCE BEGINS AT AA 4 OF PROTEIN"

( x i ) SEQUENCE DESCRIPTION: SEQ ID NO:20:

Glu Leu Met Pro Pro Gly Asp Asn Phe Asp Leu Glu Lys Tyr Phe Ser
1               5                       10                      15

Ile ( 2 ) INFORMATION FOR SEQ ID NO:21:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 27..32
        ( D ) OTHER INFORMATION: /note= "XhoI site"

( x i ) SEQUENCE DESCRIPTION: SEQ ID NO:21:

GAGAGAGAGA GAGAGAGAGA ACTAGTCTCG AGTTTTTTTT TTTTTTTT    49

( 2 ) INFORMATION FOR SEQ ID NO:22:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 4..9
        ( D ) OTHER INFORMATION: /note= "SphI site"

( i x ) FEATURE:
        ( A ) NAME/KEY: modified_base
        ( B ) LOCATION: 11
        ( D ) OTHER INFORMATION: /mod_base=i ( i x ) FEATURE:
        ( A ) NAME/KEY: modified_base
        ( B ) LOCATION: 14
        ( D ) OTHER INFORMATION: /mod_base=i ( i x ) FEATURE:
        ( A ) NAME/KEY: modified_base
        ( B ) LOCATION: 17
        ( D ) OTHER INFORMATION: /mod_base=i ( x i ) SEQUENCE DESCRIPTION: SEQ ID NO:22:

GCGGCATGCC NCCNGGNGAY AAYTTYGA    28

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Met Pro Pro Gly Asp Asn Phe Asp
1               5

( 2 ) INFORMATION FOR SEQ ID NO:24:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i x ) FEATURE:
  ( A ) NAME/KEY: modified_base
  ( B ) LOCATION: 12
  ( D ) OTHER INFORMATION: /mod_base=i ( x i ) SEQUENCE DESCRIPTION: SEQ ID NO:24:

AACTTTGAYY TNGARAARTA YTT      23

( 2 ) INFORMATION FOR SEQ ID NO:25:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:25:

Asn Phe Asp Leu Glu Lys Tyr Phe
 1               5

( 2 ) INFORMATION FOR SEQ ID NO:26:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i x ) FEATURE:
  ( A ) NAME/KEY: modified_base
  ( B ) LOCATION: one-of(6, 9, 12, 37)
  ( D ) OTHER INFORMATION: /mod_base=i ( x i ) SEQUENCE DESCRIPTION: SEQ ID NO:26:

ATGCCNCCNG GNGAYAAYTT TGAYYTNGAG AAGTAYTT      38

( 2 ) INFORMATION FOR SEQ ID NO:27:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:27:

Met Pro Pro Gly Asp Asn Phe Asp Leu Glu Lys Tyr Phe
 1               5                  10

( 2 ) INFORMATION FOR SEQ ID NO:28:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i x ) FEATURE:
  ( A ) NAME/KEY: misc_feature
  ( B ) LOCATION: 17..22
  ( D ) OTHER INFORMATION: /note= "XhoI site"

( x i ) SEQUENCE DESCRIPTION: SEQ ID NO:28:

GAGAGAGAGA ACTAGTCTCG AG　　22

( 2 ) INFORMATION FOR SEQ ID NO:29:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:29:

TATCACTCTG AACTCAAGTG　　20

( 2 ) INFORMATION FOR SEQ ID NO:30:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:30:

TTACCGCCGT TTCCATTTGG　　20

( 2 ) INFORMATION FOR SEQ ID NO:31:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:31:

TTACTTCAAA GTTGCACC　　18

( 2 ) INFORMATION FOR SEQ ID NO:32:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:32:

GCAACATGAA GGTGATCATT GCAGCAAC　　28

( 2 ) INFORMATION FOR SEQ ID NO:33:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( i x ) FEATURE:
  ( A ) NAME/KEY: misc_feature
  ( B ) LOCATION: 7..12
  ( D ) OTHER INFORMATION: /note= "HindIII site"

( i x ) FEATURE:
  ( A ) NAME/KEY: misc_feature
  ( B ) LOCATION: 13..16
  ( D ) OTHER INFORMATION: /note= "Kozak site"

( i x ) FEATURE:
  ( A ) NAME/KEY: misc_feature
  ( B ) LOCATION: 17..37
  ( D ) OTHER INFORMATION: /note= "portion of the sequence
   matching one or the other strand of the orignal
   cDNA clone"

( x i ) SEQUENCE DESCRIPTION: SEQ ID NO:33:

GCGATAAAGC TTCCACCATG AAGGTGATCA TTGCAGC    37

( 2 ) INFORMATION FOR SEQ ID NO:34:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 7..12
        ( D ) OTHER INFORMATION: /note= "HindIII site"

( i x ) FEATURE:
        ( A ) NAME/KEY: misc_feature
        ( B ) LOCATION: 11..30
        ( D ) OTHER INFORMATION: /note= "portion of the sequence matching one or the other strand of the original cDNA"

( x i ) SEQUENCE DESCRIPTION: SEQ ID NO:34:

GCGATAAAGC TTATTACTTC ATGTTATCAC    30

( 2 ) INFORMATION FOR SEQ ID NO:35:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

ACCAGAAAGT TAACTGG    17

( 2 ) INFORMATION FOR SEQ ID NO:36:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

CCTAGTTTGT GGTTGTCC    18